US009186190B2

(12) United States Patent
Zhou et al.

(10) Patent No.: US 9,186,190 B2
(45) Date of Patent: Nov. 17, 2015

(54) FUNCTIONALIZED NANODIAMOND REINFORCED BIOPOLYMERS

(75) Inventors: Gongyao Zhou, Wilmington, DE (US); Peter I. Lelkes, Cherry Hill, NJ (US); Yury Gogotsi, Ivyland, PA (US); Vadym Mochalin, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 529 days.

(21) Appl. No.: 13/498,436

(22) PCT Filed: Oct. 1, 2010

(86) PCT No.: PCT/US2010/051176

§ 371 (c)(1), (2), (4) Date: Jul. 5, 2012

(87) PCT Pub. No.: WO2011/041714

PCT Pub. Date: Apr. 7, 2011

(65) Prior Publication Data

US 2012/0271361 A1 Oct. 25, 2012

Related U.S. Application Data

(60) Provisional application No. 61/248,202, filed on Oct. 2, 2009.

(51) Int. Cl.

| | |
|---|---|
| ***A61B 17/86*** | (2006.01) |
| ***A61K 47/02*** | (2006.01) |
| ***A61K 47/30*** | (2006.01) |
| ***A61L 31/12*** | (2006.01) |

(52) U.S. Cl.

CPC ............. *A61B 17/866* (2013.01); *A61L 31/125* (2013.01); *A61L 31/128* (2013.01); *A61B 17/864* (2013.01); *A61L 2400/12* (2013.01)

(58) Field of Classification Search

CPC .............. A61L 2400/12; A61L 31/128; A61L 2400/23; A61L 31/125; C01B 31/065; A61B 17/864; A61B 17/866

See application file for complete search history.

(56) References Cited

U.S. PATENT DOCUMENTS

| | | | | |
|---|---|---|---|---|
| 7,294,340 | B2 | 11/2007 | Sung et al. | |
| 2003/0036800 | A1 | 2/2003 | Meredith | |
| 2005/0158549 | A1 | 7/2005 | Khabashesku et al. | |
| 2008/0033093 | A1 * | 2/2008 | Menceloglu et al. | 524/445 |
| 2008/0069857 | A1 | 3/2008 | Yeo et al. | |
| 2008/0255213 | A1 | 10/2008 | Miller et al. | |
| 2009/0157194 | A1 | 6/2009 | Shikinami | |
| 2009/0187155 | A1 | 7/2009 | Razavi | |
| 2009/0202644 | A1 | 8/2009 | Gogotsi et al. | |

FOREIGN PATENT DOCUMENTS

| | | | |
|---|---|---|---|
| WO | WO 2006096203 | A2 * | 9/2006 |
| WO | WO 2006113192 | A2 * | 10/2006 |
| WO | WO 2007022200 | A2 * | 2/2007 |
| WO | WO 2007105600 | A1 * | 9/2007 |
| WO | 2009/038850 | | 3/2009 |

OTHER PUBLICATIONS

Lisichkin et al., Russian Chemical Bulletin, International Edition, 2006, 55(12), 2212-2219.*

Mochalin, et al., "Wet Chemistry Route to Hydrophobic Blue Fluorescent Nanodiamond," *J. Am. Chem. Soc.*, 2009, 131:4594-4595.

Mochalin, et al., "High Temperature Functionalization and Surface Modification of Nanodiamond Powders," *Mater. Res. Soc. Symp. Proc.*, 2008, vol. 1039, 11 pages.

Navarro, et al., "Biomaterials in orthopaedics," *J. R. Soc. Interface*, 2008, 5:1137-1158.

International Search Report and Written Opinion received for PCT/US10/51176, filed Oct. 1, 2010.

Agrawal et al., "Biodegradable polymeric scaffolds for musculoskeletal tissue engineering," J Biomed Mater Res., 55:141-150 (2001).

Zhang et al., "Nanotechnology and nanomaterials: Promises for improved tissue regeneration," Nano Today, 4:66-80 (2009).

Mei et al., "Improved Biological Characteristics of Poly(L-Lactic Acid) Electrospun Membrane by Incorporation of Multiwalled Carbon Nanotubes/Hydroxyapatite Nanoparticles," Biomacromolecules, 8:3729-3735 (2007).

Hanemann et al., "Polymer-Nanoparticle Composites: From Synthesis to Modern Applications," Materials, 3:3468-3517 (2010).

Deng et al., "Preparation and mechanical properties of nanocomposites of poly(D, L-lactide) with Ca-deficient hydroxyapatite nanocrystals," Biomaterials, 22:2867-2873 (2001).

Bourmaud et al., "Investigations on mechanical properties of poly(propylene) and poly(lactic acid) reinforced by miscanthus fibers," Composites Part A, 39:1444-1454 (2008).

Oksman et al., "Natural fibres as reinforcement in polylactic acid (PLA) composites," Composites Science and Technology, 63:1317-1324 (2003).

Shi et al., "Injectable Nanocomposites of Single-Walled Carbon Nanotubes and Biodegradable Polymers for Bone Tissue Engineering," Biomacromolecules, 7:2237-2242 (2006).

Karbushev et al., "Preparation of Polymer-Nanodiamond Composites with Improved Properties," Advanced Materials Research, 59:275-278 (2009).

Behler et al., "Nanodiamond—Polymer Composite Fibers and Coatings," ACS Nano, 3(2):363-369 (2009).

Wang et al., "In-Situ Nanocomposite Synthesis: Arylcarbonylation and Grafting of Primary Diamond Nanoparticles with a Poly(ether-ketone) in Polyphosphoric Acid," Macromolecules, 42:114-124 (2009).

* cited by examiner

*Primary Examiner* — Abigail Fisher

(74) *Attorney, Agent, or Firm* — Saul Ewing LLP; Kathryn Doyle; Brian R. Landry

(57) ABSTRACT

The present invention includes a composition for implantation in a patient, comprising surface-functionalized nanodiamonds and at least one biodegradable biocompatible polymer. The present invention also includes a surgical fixation device for use in a patient.

20 Claims, 25 Drawing Sheets

FIG. 4

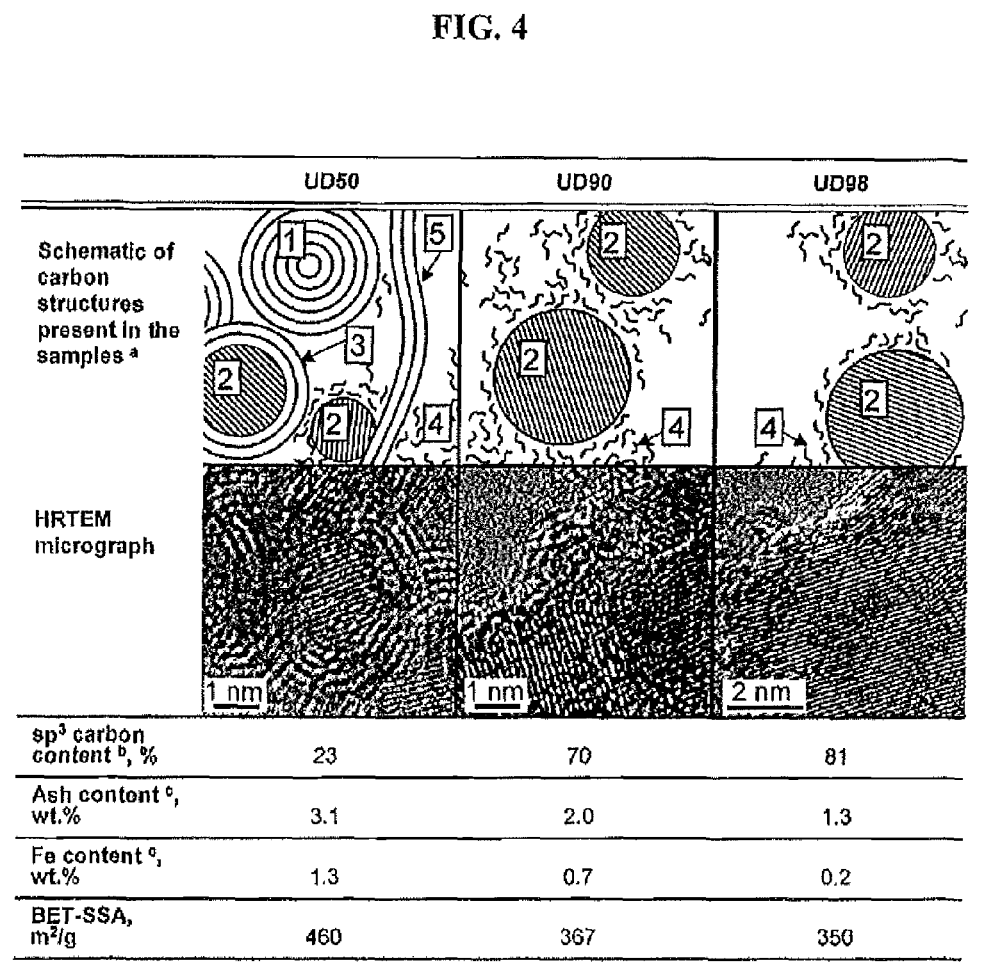

| | UD50 | UD90 | UD98 |
|---|---|---|---|
| Schematic of carbon structures present in the samples [a] | | | |
| HRTEM micrograph | 1 nm | 1 nm | 2 nm |
| $sp^3$ carbon content [b], % | 23 | 70 | 81 |
| Ash content [c], wt.% | 3.1 | 2.0 | 1.3 |
| Fe content [c], wt.% | 1.3 | 0.7 | 0.2 |
| BET-SSA, $m^2/g$ | 460 | 367 | 350 |

(A)

(B)

| Sample Composition | Young's Modulus (GPa) | Increase (%) | Hardness (GPa) | Increase (%) |
|---|---|---|---|---|
| pure PLLA | 2.6±0.1* | 0 | 0.05±0.01 | 0 |
| 1 % wt ND-ODA/PLLA | 5.3±0.2 | 107 | 0.21±0.01 | 320 |
| 3 % wt ND-ODA/PLLA | 5.5±0.3 | 113 | 0.25±0.01 | 400 |
| 5 % wt ND-ODA/PLLA | 5.9±0.3 | 129 | 0.26±0.01 | 420 |
| 7 % wt ND-ODA/PLLA | 6.8±0.5 | 165 | 0.31±0.06 | 520 |
| 10 % wt ND-ODA/PLLA | 7.9±0.1 | 206 | 0.46±0.05 | 820 |
| 1 % wt UD90/PLLA | 2.8±0.2 | 9 | 0.12±0.01 | 140 |
| 3 % wt UD90/PLLA | 2.7±0.1 | 5 | 0.11±0.01 | 120 |

*-Data are expressed as means ±SD (n=10)

FIG. 25

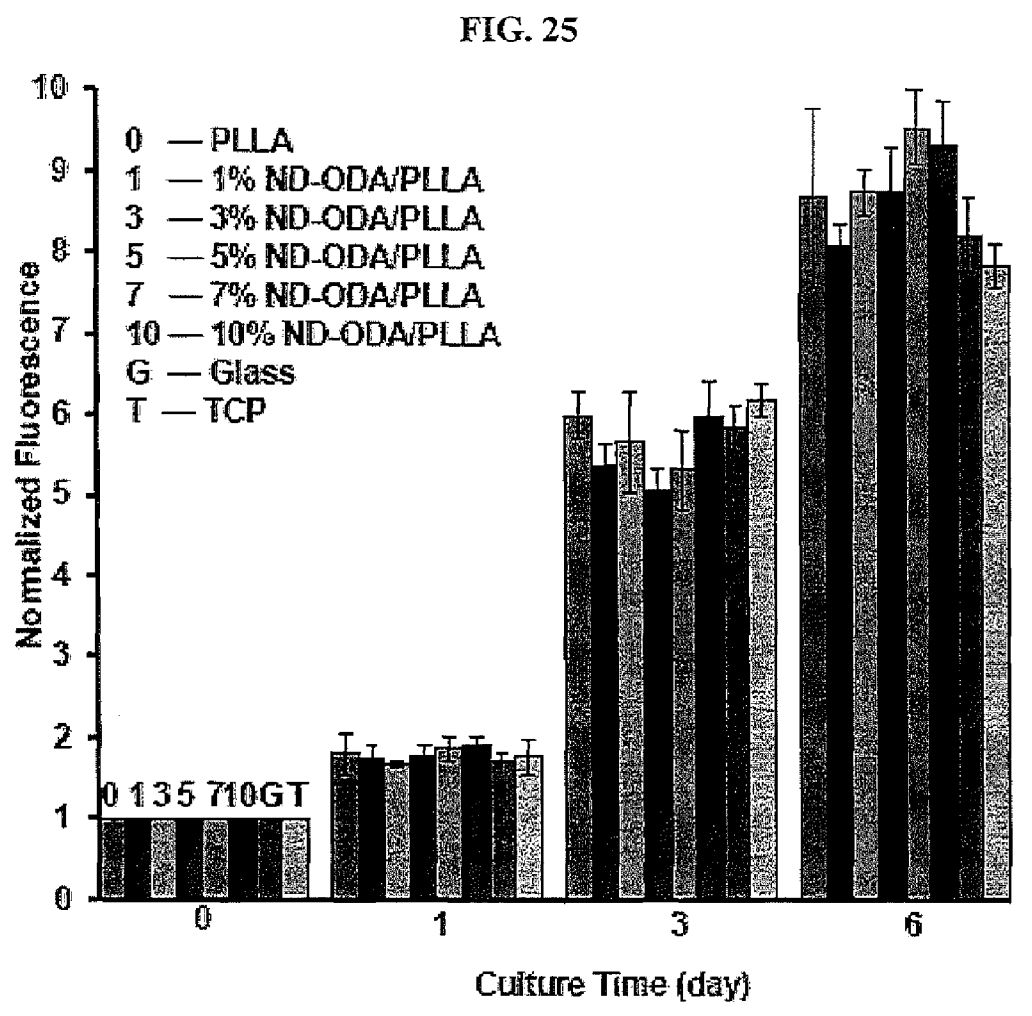

0 — PLLA
1 — 1% ND-ODA/PLLA
3 — 3% ND-ODA/PLLA
5 — 5% ND-ODA/PLLA
7 — 7% ND-ODA/PLLA
10 — 10% ND-ODA/PLLA
G — Glass
T — TCP 0 1 3 5 7 10 G T Normalized Fluorescence Culture Time (day)

FUNCTIONALIZED NANODIAMOND REINFORCED BIOPOLYMERS

CROSS-REFERENCE TO RELATED APPLICATIONS

The present application is a 35 U.S.C. §371 national phase application from, and claiming priority to, International Application No. PCT/US2010/051176, filed Oct. 1, 2010, and published under PCT Article 21(2) in English, which claims priority to U.S. Provisional Application No. 61/248,202, filed Oct. 2, 2009, which applications are incorporated by reference herein in their entireties.

BACKGROUND OF THE INVENTION

Medical problems that affect bones, including fractures, degenerative diseases and inflammatory syndromes, impact millions of people worldwide. Bone fractures, lower back pain, osteoporosis, scoliosis and other musculoskeletal problems generally require orthopedic intervention with the use of permanent or temporary medical surgical fixation devices. The properties of these fixation devices play a key role in determining the success and recovery time for the medical procedures.

Surgical fixation devices, including plates, screws, pins, rods, anchors and staples, are used in orthopedic surgery procedures, such as: bone fracture fixation (Weiler et al., 1988, Am. J. Sports Med. 26(1):119-28); autograft ankle stabilization (Jeys et al., 2004, Am. J. Sports Med. 32(7): 1651-59); reconstruction surgery of the anterior cruciate ligament (ACL) and the posterior cruciate ligament (PCL) (Nakano et al., 2000, Clin. Biomech. 5(3):188-95); replacement of the intervertebral discs (Ella et al., 2005, J. Mat. Sci.-Mat. Med. 16(7):655-62); and posterior spinal fixation (Evans et al., 2002, J. Mat. Sci.-Mat. Med. 13(12):1143-45).

Metal surgical fixation devices are often used to replace damaged or missing bone tissue due to their high initial fixation strength (Kurosaka et al., 1987, Am. J. Sports Med. 15(3):225-29; Lambert, 1983, Clin. Orthop. Rel. Res. 172: 85-89; Shelbourne & Nitz, 1990, Am. J. Sports Med. 18(3): 292-99). However, metallic implant devices are not degradable, leaving cavitations in the bone once the devices are removed.

In recent years, surgical fixation devices prepared with biocompatible polymers have been investigated as potential replacements of metallic fixation devices. Biocompatible polymers have the potential to revolutionize biomedical engineering as scaffolds for hard and soft tissues, such as bone and blood vessels. Compared with conventional metal fixation devices, biocompatible polymer-based fixation devices have the advantages of causing no long-term implant palpability, no long-term temperature sensitivity, no stress shielding and no interference with post-operative diagnostic imaging. These advantages may lead to better bone healing, reduced patient trauma, reduced cost, elimination of need for a subsequent surgery for implant removal, and fewer complications from infections.

However, biocompatible polymer-based fixation devices still face challenges. The polymer or composite used in the devices should have good biocompatibility with the surrounding tissue and have mechanical properties similar to the bone tissue being replaced. Furthermore, the polymer or composite should be biodegradable so that it is gradually replaced by newly grown tissue (Claes et al., 1986, Akt. Traumatol. 16:74-77; Rokkanen et al., 1985, Lancet 1(8443):1422-24). Most current biocompatible polymers are not strong enough from a mechanical standpoint, especially when used as surgical fixation devices and bone scaffolds. Furthermore, current biocompatible polymer-based surgical fixation devices do not actively promote bone healing and regrowth, leaving voids in the tissue once the implanted device is fully degraded. There is thus a need to identify a polymer or composite material that combines structural strength and bone tissue regrowth stimulation.

Nanosized diamond powders (also known as nanodiamonds or NDs) are produced by detonation synthesis in large volumes (Shenderova & McGuire, "Nanocrystalline Diamond," in "Nanomaterials handbook," Y. Gogotsi, Ed., 2006, CRC Taylor and Francis: Boca Raton, p. 203-37) and represent a new class of relatively inexpensive carbon nanomaterial with a broad range of potential applications, including composite materials. NDs have been used as components of sorbents, lubricating and polishing compositions and as additives to electrolytic and electroless deposition baths.

NDs are composed of particles of about 5 nm in diameter and consist of an inert diamond core terminated with surface chemical groups such as C═O, COOH, and OH (Lam et al., 2008, ACS Nano 2(10):2095-2102), as shown in FIG. 1. When originally synthesized, the diamond core is often surrounded by graphene shells and amorphous carbon (FIGS. 1*a* and 1*b*; Osswald et al., 2006, J. Am. Chem. Soc. 128(35): 11635-42).

NDs are a member of the nanocarbon family, but differ from other well-known nanomaterials, such as fullerenes and carbon nanotubes (Shenderova et al., 2002, Crit. Rev. Solid State Mat. Sci. 27(3-4):227-356). NDs exhibit the excellent mechanical, thermal and electrical properties of diamond at nanoscale, and actually outperform carbon nanotubes (CNTs) and other known materials. For example, the thermal conductivity of nanodiamonds (~2000 $W \cdot m^{-1} \cdot K^{-1}$) is of the same order as the highest reported for CNTs (6600 $W \cdot m^{-1} \cdot K^{-1}$) (Berber et al., Phys. Rev. Lett. 84(20):4613-16). However, in contrast to carbon nanotubes, ND is a good insulator.

An attractive characteristic of NDs is their relative lack of toxicity and their biocompatibility. NDs have recently been reported to be the least toxic of all carbon nanomaterials (Puzyr et al., 2007, Diamond Relat. Mater. 16:2124-28; Huang et al., 2007, Nano. Lett. 7(11):3305-14; Mitura et al., 2006, J. Achiev. Mat. Manuf. Eng. 16(1-2):9-16; Bakowicz-Mitura, 2007, Surf. Coat, Technol. 201(13):6131-35; Lam et al., 2008, ACS Nano 2(10):2095-2102; Liu et al., 2007, Nanotechnol. 18(5):55102; Schrand et al., 2007, J. Phys. Chem. B 111(1):2-7; Puzyr et al., 2007, Diamond Relat. Mater. 16:2124-28). In contrast, the toxicity of CNTs is still debatable and raises concerns regarding their use in biological applications (Cherukuri et al., 2004, J. Am. Chem. Soc. 126 (48):15638-39; Cherukuri et al., 2006, Proc. Natl. Acad. Sci. U.S.A. 103:18882-86).

The small particle size and the low toxicity of NDs make them desirable for biological applications. Still, many potential applications of NDs, including in biomedical and composite materials, remain unexplored.

There remains a need in the art to identify novel materials that are compatible with biological systems and may have used in biomedical applications, such as orthopedic surgery. The present invention fulfills these needs.

BRIEF SUMMARY OF THE INVENTION

In one aspect, the invention includes a nanocomposite material comprising surface-functionalized nanodiamonds and at least one biodegradable biocompatible polymer.

In one embodiment, the at least one biodegradable biocompatible polymer is selected from the group consisting of polyglycolic acid, polylactic acid, poly-L-lactic acid, poly-D/L-lactic acid with polyglycolic acid, poly-L-lactic acid-co-glycolic acid, PDLLA with bioactive glass, PLGA with bioactive glass, poly-L-lactic acid with β-tricalcium phosphate, poly-L-lactic acid with hydroxyapatite, polydioxanone, polyethylene glycol, poly(s-caprolactone), polycaprolactone with alginate, polyhydroxybutyrate, polycarbonate, N-vinyl pyrrolidone copolymers, polyorthoester, chitosan, poly(2-hydroxyethyl-methacrylate), hyaluronic acid and a hydrogel. In another embodiment, the at least one biodegradable biocompatible polymer is selected from the group consisting of polyglycolic acid, polylactic acid, poly-L-lactic acid, poly-D/L-lactic acid with polyglycolic acid, poly-L-lactic acid-co-glycolic acid, poly-L-lactic acid with β-tricalcium phosphate, and poly-L-lactic acid with hydroxyapatite.

In one embodiment, the surface-functionalized nanodiamonds are prepared from chemically-active nanodiamonds. In another embodiment, the chemically-active nanodiamonds comprise chemical groups selected from the group consisting of carboxylate, carbonyl, amino and hydroxyl. In yet another embodiment, the surface-functionalized nanodiamonds are prepared by peptide bond formation between an amine and a carboxylate group of the chemically-active nanodiamonds. In yet another embodiment, the amine is selected from the group consisting of octylamine, decylamine, undecylamine, dodecylamine, tridecylamine, tetradecylamine, pentadecylamine, hexadecylamine, heptadecylamine, dodecadecylamine, nonadecylamine and eicosylamine. In yet another embodiment, the amine is octadecylamine.

In one embodiment, the at least one biodegradable biocompatible polymer forms hydrogen-bond interactions with the surface-functionalized nanodiamonds. In yet another embodiment, the at least one biodegradable biocompatible polymer forms a covalent bond with the surface-functionalized nanodiamonds. In yet another embodiment, the covalent bond is an amide bond formed between a carboxylate group of the at least one biodegradable biocompatible polymer and an amino group of the surface-functionalized nanodiamonds. In yet another embodiment, the at least one biodegradable biocompatible polymer is selected from the group consisting of polyglycolic acid, polylactic acid, poly-L-lactic acid, poly-D/L-lactic acid with polyglycolic acid, poly-L-lactic acid-co-glycolic acid, poly-L-lactic acid with β-tricalcium phosphate, and poly-L-lactic acid with hydroxyapatite.

In one embodiment, the material comprises 0.1% to 50% of the surface-functionalized nanodiamonds. In another embodiment, the material further comprises a composition comprising at least one bioactive agent selected from the group consisting of a bone healing drug, growth factor, bone cell, bone stem cell, antibiotic, and anti-inflammatory drug.

In another aspect, the invention comprises a surgical fixation screw. The screw comprises an intercoruective porous shell, wherein the shell comprises a nanocomposite material comprising functionalized nanodiamonds and at least one biodegradable biocompatible polymer. The screw further comprises a hollow core within the shell, wherein the hollow core is closed on the posterior end of the screw and open on the anterior end of the screw.

In one embodiment, the hollow core is optionally filled with a composition comprising at least one bioactive agent selected from the group consisting of a bone healing drug, growth factor, bone cell, bone stem cell, antibiotic, and anti-inflammatory drug. In another embodiment, the posterior end is tapered with respect to the anterior end. In yet another embodiment, the screw has full-length taper. In yet another embodiment, the anterior end is without head. In yet another embodiment, the posterior end is rounded and blunt. In yet another embodiment, the shell has controllable varying coarseness, whereby phase of the nanocomposite material around the hollow core is coarser than phase of the nanocomposite material on outside surface of the screw. In yet another embodiment, the controllable varying coarseness is achieved through injection molding.

In yet another aspect, the invention includes a method of performing an orthopedic surgery procedure in a patient. The method of the invention comprises the steps of:

(a) inserting a surgical fixation screw in at least one orifice of a bone or tissue of the patient. The screw comprises:

(a.1) an interconnective porous shell, wherein the shell comprises a nanocomposite material comprising functionalized nanodiamonds and at least one biodegradable biocompatible polymer, and (a.2) a hollow core within the shell, wherein the hollow core is closed on the posterior end of the screw and open on the anterior end of the screw, and (b) filling the hollow core of the screw with a composition comprising at least one bioactive agent selected from the group consisting of a bone healing drug, growth factor, bone cell, bone stem cell, antibiotic, and anti-inflammatory drug.

In one embodiment, the at least one biodegradable biocompatible polymer is selected from the group consisting of polyglycolic acid, polylactic acid, poly-L-lactic acid, poly-D/L-lactic acid with polyglycolic acid, poly-L-lactic acid-co-glycolic acid, PDLLA with bioactive glass, PLGA with bioactive glass, poly-L-lactic acid with β-tricalcium phosphate, poly-L-lactic acid with hydroxyapatite, polydioxanone, polyethylene glycol, poly(ϵ-caprolactone), polycaprolactone with alginate, polyhydroxybutyrate, polycarbonate, N-vinyl pyrrolidone copolymers, polyorthoester, chitosan, poly(2-hydroxyethyl-methacrylate), hyaluronic acid and a hydrogel. In another embodiment, the posterior end is tapered with respect to the anterior end. In yet another embodiment, the screw has full-length taper. In yet another embodiment, the anterior end is without head. In yet another embodiment, the posterior end is rounded and blunt. In yet another embodiment, the shell has controllable varying coarseness, such that phase of the nanocomposite material around the hollow core is coarser than phase of the nanocomposite material on outside surface of the screw. In yet another embodiment, the controllable varying coarseness is achieved through injection molding.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1*a*-1*d*, is a series of high resolution transmission electron microscope (HR-TEM) images (FIGS. 1*a* & 1*c*) and PM3 optimized molecular models (FIGS. 1*b* & 1*d*) illustrating the structure of as-produced (FIGS. 1*a* & 1*b*) and oxidized (FIGS. 1*c* & 1*d*) ND particles.

FIGS. 2*a*-2*d*, is a schematic representation of the incorporation of 5-nm ND particles into polymer-matrix composites. FIG. 2*a* depicts agglomerated particles, which lead to property degradation. FIG. 2*b* depicts inert filler, without chemical interactions with the polymer. FIG. 2*c* depicts polymer that is covalently bonded to disordered carbon shells. FIG. 2*d* depicts polymer chains that are covalently bonded to the diamond surface.

FIGS. 3*a*-3*b*, is a schematic representation of covalently bound polymer-matrix composites using CNTs (FIG. 3*a*) and NDs (FIG. 3*b*) as a filler.

FIG. 4 is a schematic representation of the structure and selected physical properties of nanodiamond samples. The following legends apply: (a) as determined using transmission electron microscope (TEM): (b) as determined using soft X-ray absorption near-edge structure (XANES); (c) as reported by supplier NanoBlox, Inc. (Boca Raton, Fla., USA). The following codes apply: (1) carbon onion; (2) nanodiamond; (3) fullerenic shell; (4) amorphous carbon; (5) graphite ribbon.

FIGS. 10*a*-10*d*, is a series of images comparing the nanodiamond dispersion in PLLA. The dispersion of ND-ODA in PLLA/chloroform solution was stable (day 1, FIG. 10*a*; and day 9, FIG. 10*b*). In contrast, most of NDs precipitated from PLLA/chloroform solution after one day (day 1, FIG. 10*c*; and day 2, FIG. 10*d*).

FIGS. 12*a*-12*b*, is a series of graphs depicting the hardness and Young's modulus of PA-11/ND films with different contents of nanodiamond (FIG. 12*a*). Indentation curves for epoxy/ND composites with different contents of nanodiamond are depicted in FIG. 12*b*.

FIGS. 13*a*-13*b*, is a series of images depicting the bisbenzimide nuclear staining of adherent U2OS cells following 72 hours of seeding on pure PLLA (FIG. 13*a*, 100×) and ND-ODA/PLLA composite (0.5% wt ODA) (FIG. 13*b*, 100×) scaffolds. Images were captured by imaging the surface of a strut on the outside of the scaffolds.

FIGS. 15*a*-15*b*, is a series of images of different porous structures obtained through different processing conditions: FIG. 15*a*, without dwell time inside the intruder; and FIG. 15*b*, with dwell time inside the intruder.

FIG. 18*a*-18*d*, illustrates the composites of the invention. FIG. 18*a* is a schematic illustration of the manufacturing and use of ND-ODA/PLLA composites. FIG. 18*b* is an illustrative molecular model of an ND-ODA particle. FIG. 18*c* is an illustrative comparison between $^{13}C$ MAS NMR spectra for UD90-ODA obtained via direct polarization and $^{1}H$ to $^{13}C$ cross polarization. FIG. 18*d* is a representation of a high resolution TEM illustrating an ND-ODA cluster where pristine nanodiamond particles are surrounded by ODA chains.

FIGS. 19*a*-19*d*, illustrates the characterization of the ND-ODA particles. FIG. 19*a* is a graph illustrating the ND-ODA particle size in PLLA/chloroform solution. Particle size measurement showed 32 nm and 28 nm ND-ODA agglomerates in 1% wt (curve 1) and 10% wt (curve 2) ND-ODA/PLLA-chloroform solution, respectively. The small particle size corresponded to ND-ODA aggregates composed of less than 5 ND-ODA particles in an aggregate cross-section. FIGS. 19*b-d* illustrate low resolution TEM micrographs of ND-ODA/PLLA thin cross-sections, suggesting a uniform dispersion of small clusters of ND-ODA in the PLLA matrix at concentrations 1% (FIG. 19*b*), 3% (FIG. 19*c*), and 10% (FIG. 19*d*). No micron-sized aggregates were observed. With the increasing ND-ODA concentration, interconnected chains were formed between ND-ODA clusters (FIG. 19*d*).

FIGS. 20*a-f*, illustrates representative load-displacement curves (FIG. 20*a*) and stress-strain curves (FIG. 20*b*) of pure PLLA and ND-ODA/PLLA composites with 1% wt and 10% wt of ND-ODA. FIGS. 20*a* and 20*b* illustrate that the increase in ND-ODA content results in a pronounced reduction of creep and leads to an increase in hardness and Young's modulus of the nanocomposites. Comparison of Vickers indents on pure PLLA (FIG. 20*c*) and 10% ND-ODA/PLLA composite (FIG. 20*d*) provided a further evidence of a dramatic improvement in the elastic recovery of the ND-ODA/PLLA samples. FIG. 20*e* illustrates XRD patterns of pure PLLA and 10% wt ND-ODA/PLLA thin films. Upper curve in FIG. 20*e* illustrates the XRD of a pure PLLA film. Bottom curve in FIG. 20*e* illustrates the XRD of 10% wt of an ND-ODA/PLLA film. Both patterns showed Bragg peaks of PLLA, which are, in case of the pure PLLA film, seen atop of a strong amorphous halo indicating less crystallinity of PLLA as compared to the 10% wt ND-ODA/PLLA, Narrower and more intense peaks of 10% wt ND-ODA/PLLA also confirmed the higher crystallinity of the composite. FIG. 20*f* is a table summarizing the mechanical properties determined by depth sensing indentation.

FIGS. 21*a-d*, illustrates SEM images of a 10% wt ND-ODA/PLLA thin film produced through solution casting. FIG. 21*a* illustrates the porous structure of the film, which facilitates cell attachment and growth. Due to the presence of ND-ODA in the PLLA matrix around pores, the film shows blue and red fluorescence (shown as light areas in the figures reproduced herein) under excitation with 360 nm (FIG. 21*b*) and 555 nm (FIG. 21*c*). Fluorescence patterns coincided with the porous structure observed under SEM. The clear fluorescence of the 10% wt ND-ODA/PLLA scaffold (FIG. 21*d*) seen in the background of 7F2 osteoblasts after 3 days post-seeding indicated the possibility to monitor the composite degradation in situ through the fluorescence observation.

FIGS. 22*a-f*, illustrates the morphology of 7F2 osteoblasts on pure PLLA and 10% wt ND-ODA/PLLA. The morphology of these cells at 2 and 6 days of post-seeding on pure PLLA (FIGS. 22*a* and 22*c*) and 10% wt ND-ODA/PLLA (FIGS. 22*b* and 22*d*) are illustrated. Cell morphology of 2 days post-seeding on PLLA (FIG. 22*a*) and 10% wt ND-ODA/PLLA (FIG. 22*b*) suggests that the attachment of osteoblasts on the surface of 10% wt ND-ODA/PLLA scaffold was as good as on the surface of a pure PLLA scaffold. Staining for nuclei was bis-benzimide (blue) and for actin cytoskeleton-phalloidin (red). SEM images of 7F2 grown on the different scaffolds after 6 days post-seeding: osteoblasts spread to confluence similarly on the surface of pure PLLA (FIG. 22*e*) and 10% wt ND-ODA/PLLA (FIG. 22*f*) scaffolds.

FIG. 25 is a bar graph illustrating biocompatibility test for ND-ODA/PLLA composites, Normalized increase in AB readings was monitored for 6 days in vitro 7F2 cell culture on pure PLLA, ND-ODA/PLLA (1-10% wt of ND-ODA), and control glass and TCP substrates. Metabolic activities were measured by AB assay every three days following the 24 h seeding period. The data were normalized to the AB fluorescence reading at day 0. Error bars represent the standard deviation from the mean for each sample (n=6).

DETAILED DESCRIPTION OF THE INVENTION

Figure 1:
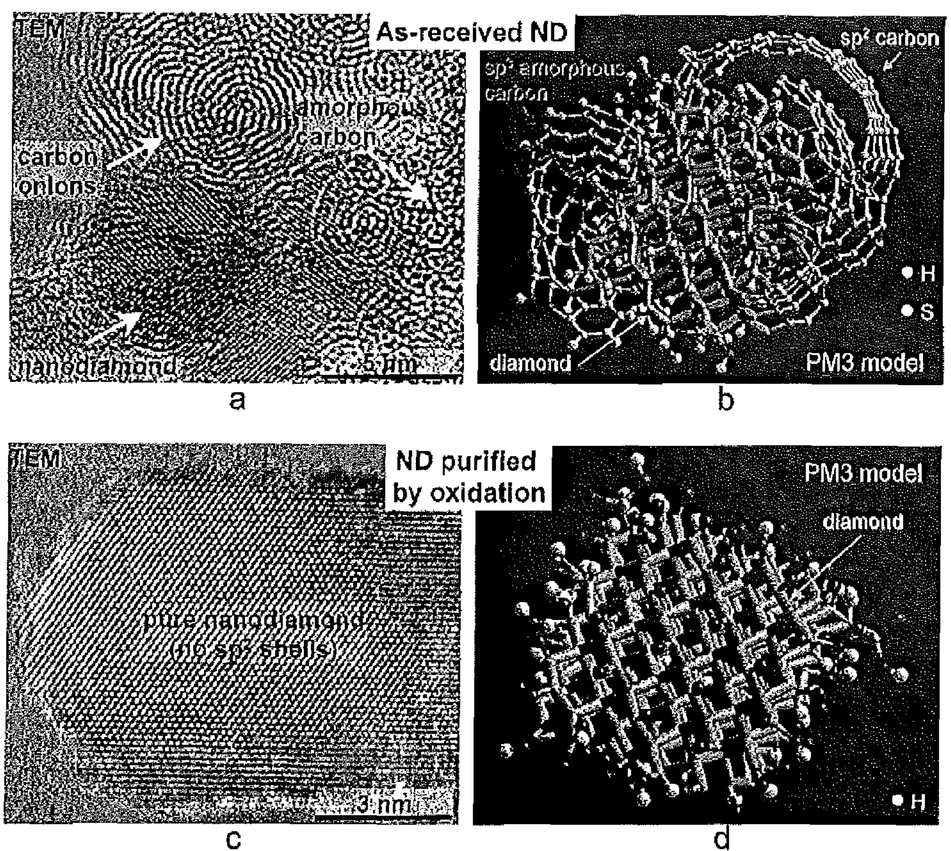
FIG. 1, comprising

The present invention relates to the discovery that a novel biomedical nanocomposite material comprising a biodegradable biocompatible polymer and surface-functionalized nanodiamonds may be utilized for the development of scaffolds and surgical fixation devices for bone repair. These novel materials are strong from a mechanical standpoint and suitable for use in surgical fixation devices and bone scaffolds. These novel materials are biocompatible and biodegradable, and preferably stimulate the regeneration of the original biological material that is being replaced, avoiding cumbersome and potentially problematic follow-up procedures.

In one aspect, the invention provides a composition comprising a biodegradable biocompatible polymer and surface-functionalized nanodiamonds for implantation in a patient. The chemical moieties located on the surface of the nanodiamonds interact with the polymer, ensuring that the nanodiamond particles are well dispersed within the polymer-nanodiamond composite. Optionally, the composition further comprises at least one bioactive agent selected from the group consisting of a bone healing drug, growth factor, bone cell, bone stem cell, antibiotic, and anti-inflammatory drug. These bioactive agents may accelerate bone healing, bone growth, tissue growth and/or surgical recovery.

In another aspect, the invention provides a surgical fixation device for use in a patient, wherein the device comprises a composition comprising a biodegradable biocompatible polymer and surface-functionalized nanodiamonds. The device is comprised of materials that have a proven safety record and have sufficient mechanical strength. Optionally, the devise further comprises at least one bioactive agent selected from the group consisting of a bone healing drug, growth factor, bone cell, bone stem cell, antibiotic, and anti-inflammatory drug. The device may further promote faster bone growth than existing devices.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used.

As used herein, the term "biocompatible polymer" refers to a polymeric material that does not cause inflammatory or immune response in the body. As used herein, the term "biodegradable polymer" refers to a polymeric material that undergoes degradation when placed inside the body and generates non-toxic degradation products, which may be eliminated by the body as such or metabolized into one or more non-toxic molecules. Non-limiting examples of biodegradable biocompatible polymers are: polyglycolide or polyglycolic acid (PGA); polylactide or polylactic acid (PLA); poly-L-lactic acid (PLLA); poly-D/L-lactic acid with polyglycolic acid (PDLLA-co-PGA); poly-L-lactic acid-co-glycolic acid (PLGA); PDLLA with bioactive glass; PLGA with bioactive glass; poly-L-lactic acid with β-tricalcium phosphate (PLLA-TCP); poly-L-lactic acid with hydroxyapatite (PLLA-HA); polydioxanone (PDS); polyethylene glycol (PEG); poly(ϵ-caprolactone) (PCL); polycaprolactone (PCL) with alginate; polyhydroxybutyrate (PHB); polycarbonate (PC); N-vinyl pyrrolidone copolymers; polyorthoester; chitosan; poly(2-hydroxyethyl-methacrylate) (PHEMA); hyaluronic acid and hydrogels.

As used herein, the terms "nanodiamond", "nanodiamond particle", "ND" and "nanosized diamond powder" are used interchangeably and refer a carbon nanomaterial composed of particles with about 5 nm in diameter consisting of an inert diamond core and surface chemical groups.

As used herein, the term "patient" refers to a human or a non-human animal. Non-human animals include, for example, livestock and pets, such as ovine, bovine, porcine, canine, feline and murine mammals, as well as reptiles, birds and fish. Preferably, the patient is human.

Biodegradable Polymers for Use in Surgical Fixation Devices

Increased interest in biodegradable surgical tools for bone, ligament, tendon and graft fixations has led to the development of surgical fixation devices made of biopolymeric material. Biodegradable polymers of synthetic and natural origin, such as, but not limited to, polyglycolide or polyglycolic acid (PGA), polylactide or polylactic acid (PLA), poly-L-lactic acid (PLLA), poly-D/L-lactic acid with polyglycolic acid (PDLLA-co-PGA), poly-L-lactic acid-co-glycolic acid (PLGA), PDLLA with bioactive glass, PLGA with bioactive glass, poly-L-lactic acid with β-tricalcium phosphate (PLLA-TCP), poly-L-lactic acid with hydroxyapatite (PLLA-HA), polydioxanone (PDS), poly(ϵ-caprolactone) (PCL), polycaprolactone (PCL) with alginate, polyhydroxybutyrate (PHB), polycarbonate (PC), N-vinyl pyrrolidone copolymers, polyorthoester, chitosan, poly(2-hydroxyethyl-methacrylate) (PHEMA), PEG (polyethylene glycol), hyaluronic acid and other hydrogels, were extensively studied.

The concept of bioabsorbable (or biodegradable) material was introduced by Kulkarni and coworkers in the 1960s (Kulkarni et al., 1966, Arch. Surg. 93:839; Kulkarni et al., 1971, J. Biomed. Mater. Res. 5:169-181). In the last decades, these materials have been used in many orthopaedic applications such as bone substitution, repair of bone fractures (including ligament fixation), cartilage, meniscus and intervertebral disc. They are used as sutures, rods, screws, pins and plates (Ciccone et al., 2001, J. Am. Acad, Orthop. Surg. 9:280-288).

The bioabsorbable polymers included in the invention may be processed following similar procedures as those used for thermoplastics. They may be melted and extruded, molded by injection or compression or solvent cast, but the presence of moisture must be carefully controlled, because their hydrolytic sensitivity leads to a significant decrease in the material's molecular weight. Therefore, the polymer included in the invention has to be kept completely dry before thermally processing, and its contact with moisture during the processing must be avoided.

Biodegradation of the biopolymers included in the invention is mainly caused by hydrolysis of the polymer chain backbone and to a lesser extent by enzymatic activity (Vert & Li, 1992, J. Mater. Sci. Mater. Med. 3:432-446; Li & McCarthy, 1999, Biomaterials 20:35-44). Degradation times depend on multiple factors, such as polymer crystallinity, molecular weight, thermal history, porosity, monomer concentration, geometry and the location of the implant.

The biopolymers included in the invention comprise PLA, PDS, PGA, and PLGA, which are amongst the most commonly used synthetic, biodegradable polymers, with an extensive U.S. FDA approval history (Ella et al., 2005, J. Mat. Sci.-Mat. Med. 16(7):655-662; Huh et al., 2005, Drug Del. Tech. 3(5):52-58).

PGA is a highly crystalline hydrophilic polymer, which tends to lose its mechanical strength rapidly (50% loss over a period of 2 weeks). Upon implantation, PGA degrades in about 4 weeks and can be completely absorbed in 4-6 months (Grayson et al., 2005, Biomaterials 26(14):2137-2145; Ouyang et al., 2002, Mat. Sci. & Eng. C: Biomim. Supramol. Syst, 20(1-2):63-69; Zhang et al., 2006, Pol. Degr. Stab. 91(9): 1929-1936; Panyam et al., 2003, J. Contr, Rel. 92(1-2):173-187; Oh et al., 2006, J. Mat. Sci.-Mat. Medicine 17(2):131-137; Valimaa & Laaksovirta, 2004, Biomaterials 25(7-8): 1225-1232; Habraken et al., 2006, J. Biomat. Sci.-Pol. Ed. 17(9):1057-1074).

PGA is more hydrophilic and PLA has a high modulus that makes it more suitable for load-bearing applications. For PLGA copolymers, the mechanical strength and the degradation rate depend on the ratio of PLA/PGA. As the content of PLA in the PLGA copolymer increases, the copolymer becomes mechanically stronger and degrades more slowly. In the case of PLA, PLGA and PGA, the final products of the polymer degradation are the acidic monomers (lactic acid and glycolic acid, respectively) that are metabolized to ATP, water and $CO_2$ (Brady et al., 1973, J. Biomed. Mater. Res. 7:155-166). PLGA degradation is also influenced by other factors including the polymer chain length and characteristics of the surrounding medium.

Chitosan, PHEMA, PEG and hyaluronic acid are biopolymers also included in the invention. They are among the most relevant hydrogels used in the generation of biomaterials. In hydrogels the bonding of hydrophilic macromolecules by means of covalent hydrogen and ionic bonds form a three-dimensional network that is able to retain large amounts of water in their structure. These types of polymers are useful in cartilage, ligaments, tendons and intervertebral disc repair applications (Ambrosio et al., 1996, J. Mater. Sci, Mater. Med. 7:525-530). Chitosan is a weak cationic polysaccharide obtained by extensive deacetylation of chitin and composed essentially of $\beta(1\rightarrow4)$ linked glucosamine units together with some N-acetylglucosamine units.

Nanodiamonds as Fillers

Nanodiamonds (NDs) are comprised of particles that are about 5 nm in diameter. In one embodiment, the NDs used in the invention vary in diameter from 0.1 nm to 50 nm. In another embodiment, the NDs used in the invention vary in diameter from 0.5 nm to 25 nm. In yet another embodiment, the NDs used in the invention vary in diameter from 1 nm to 10 nm. In yet another embodiment, the NDs used in the invention vary in diameter from 2 nm to 8 nm. In another embodiment, the NDs used in the invention vary in diameter from 4 nm to 6 nm.

The use of NDs as fillers within the invention is advantageous because of the high matrix/filler interface area when the size of the filler particles approaches nanometer domain. By dispersing a mere 1% vol of a nanoparticle of radius ~2 nm in a polymer (interfacial thickness ~6 nm), the volume fraction occupied by the interface region is ~63%, suggesting that more than half of the composite is affected by the presence of the second-phase particles (Winey & Vaia, 2007, MRS Bulletin 32:314-319). Thus, being well dispersed, the NDs included in the invention improve properties of the composites at very low concentrations without compromising the properties of the matrix. Furthermore, the ability of nanoparticles, such as the NDs of the present invention, to penetrate through blood-brain barrier is unique and may be utilized in drug delivery systems (Kreuter, 2004, J. Nanosci. Nanotechnol. 4(5):484-488; Muller & Keck, 2004, J. Nanosci. Nanotechnol. 4(5):471-483).

Surface-Functionalized Nanodiamonds and Chemically-Active Nanodiamonds

Figure 2:
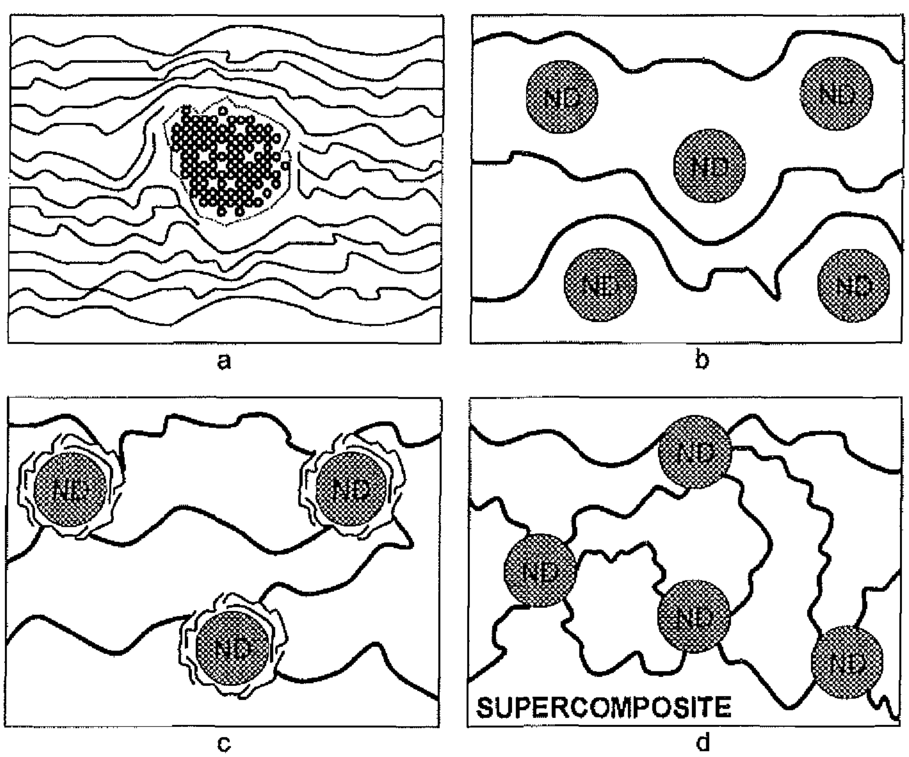
FIG. 2, comprising

Non-functionalized ND particles tend to form unusually tight aggregates (Krueger, 2008, J. Mater. Chem., 18:1485-1492). Mixing non-functionalized ND particles with a polymer typically results in poor dispersion with micron-sized nanodiamond agglomerates embedded in the matrix (FIG. 2*a*). Aggregated ND particles do not produce any property improvement for the composite, acting rather as defects and often leading to deterioration in mechanical properties.

By contrast, functionalized NDs tend not to aggregate within the composite, but rather produce a uniform distribution of NDs in the composite (FIG. 2*b*). Even when well-dispersed, however, the NDs act merely as conventional nanofillers with high hardness, performing similar to other ceramic nanoparticles (such as silica or clay) and leading to only moderate improvements in properties. In other words, good dispersion of the nanoparticles in the composite is not sufficient to ensure that the composite will have superior mechanical and thermal properties. A strong interface between the surface derivatized NDs and the matrix must also be present to ensure superior mechanical properties for the corresponding composite, and methods must be developed for the rationale modification of the surface of the ND particle.

Figure 3:
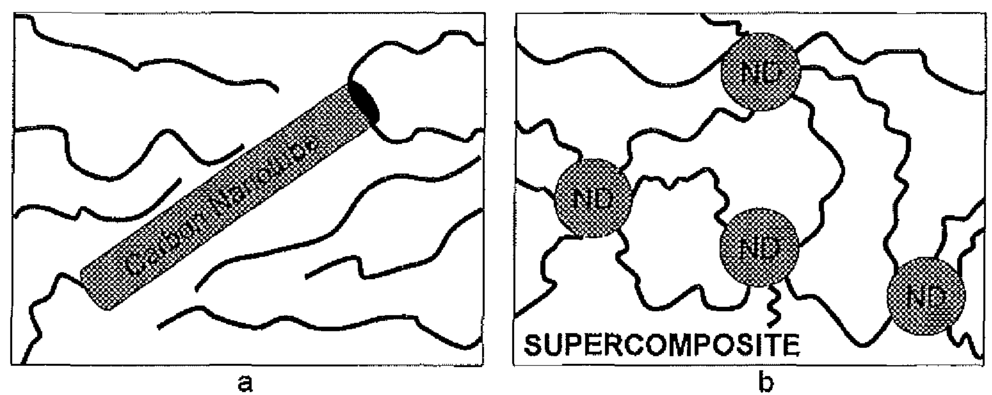
FIG. 3, comprising

In one embodiment, the strong interface between the surface derivatized NDs and the matrix is obtained by hydrogen bonds between the matrix and the surface derivatized NDs. In another embodiment, the strong interface between the surface derivatized NDs and the matrix is obtained by covalent bonds between the matrix and the surface derivatized NDs. These bonds are favored because surface derivatized NDs present a large number of functional groups on their surface and are thus able to engage in multiple interactions (FIG. 3*b*). On the other hand, CNTs have only a small number of functional groups, located at the end of the tubes, and are thus limited in their ability to interact with the matrix (FIG. 3*a*).

Nanodiamonds included in the invention may be obtained from commercial sources, such as NanoBlox, Inc. (Boca Raton, Fla., USA). This manufacturer provides nanodiamonds in different grades: UD50, UD90 and UD98 grades, wherein the number in the grade roughly corresponds to the diamond-to-graphite ratio in the material. The properties of such materials are summarized in FIG. 4.

Nanodiamonds included in the invention may present chemical groups on their surface. Such nanodiamonds are generally referred to as "chemically-active nanodiamonds." Chemically-active nanodiamonds may be manipulated by standard chemical methods to yield derivatized nanodiamonds, such as surface-functionalized nanodiamonds.

In one embodiment, surface-functionalized nanodiamonds are prepared by chemical modification of chemically-active nanodiamonds. In another embodiment, chemically-active nanodiamonds are themselves surface-functionalized nanodiamonds and are used as such within the invention.

Generation of chemically-active NDs included in the invention may be done in numerous ways, including traditional gas and wet chemistry (Osswald et al., 2006, J. Am. Chem. Soc. 128(35):11635-11642; Mochalin et al., 2007, "High Temperature Functionalization and Surface Modification of Nanodiamond Powders," In "Materials Research Society Symposium Proceedings," Boston, Mass., USA, Vol. 1039, No. 1039-P11-03). These methods allow for the generation of chemically-active nanodiamonds with different surface functional groups, which may be used as handles to introduce chemical groups on the surface of the NDs ("surface derivatization").

Among the methods for generating chemically-active NDs that are contemplated by the invention are air oxidation, hydrogenation, chlorination and ammonia treatment (Mochalin et al., 2009, Mater. Res. Soc. Symp. Proc. 1039, 1039-P11-03).

In one embodiment of the invention, the chemically-reactive NDs are prepared by air oxidation of NDs. Air oxidation (or oxidative purification) affords NDs free of amorphous and graphitic $sp^2$-bonded carbon.

Oxidative purification may be conducted under isothermal conditions using a THM600 Linkam heating stage (Linkam Scientific Instruments Ltd., Tadworth, Surrey, UK) and a tube furnace, and under non-isothermal conditions using a thermobalance (Perkin-Elmer TGA 7, Shelton, Conn., USA). Isothermal experiments include two steps: (i) rapid heating at 50° C./min to the selected temperature and (ii) isothermal oxidation for 5 hours in ambient air at atmospheric pressure. In one embodiment, the temperature range for oxidation of the ND samples investigated is 400-430° C.

Under these conditions, the purity of ND may become comparable to that of microcrystalline diamond. Metal impurities, which are initially protected by carbon shells in the commercial samples, generally become accessible after oxidation and are completely removed by further treatment in diluted acids. In addition to purification, air oxidation dramatically changes the surface chemistry of ND (FIG. 1). Oxidation of the nanodiamond particles results in nanoparticles covered by oxygen-containing functional groups such as C═O, COOH, and OH, with a decrease in the content of C—H groups. Carboxyl groups can be easily deprotonated in basic media, thus aqueous suspensions of the oxidized ND have lower aggregation tendencies at pH>7.

In another embodiment of the invention, the chemically-reactive NDs are prepared by high temperature treatment of NDs in $H_2$ atmosphere. In yet another embodiment, the high temperature treatment of NDs in $H_2$ atmosphere is for 2 hours at 800° C. This treatment increases the content of C—H-containing groups and completely removes C═O groups as a result of saturation of non-saturated bonds according to reaction (I). $H_2$ annealing may not significantly remove non-diamond carbon from the sample.

(I)

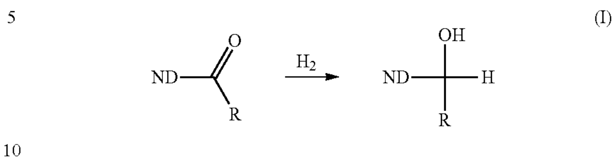

In yet another embodiment of the invention, the chemically-reactive NDs are prepared by chlorine ($Cl_2$) treatment of NDs for 1 hour at 400° C. This treatment yields acyl chlorides, as shown in reaction (II):

(II)

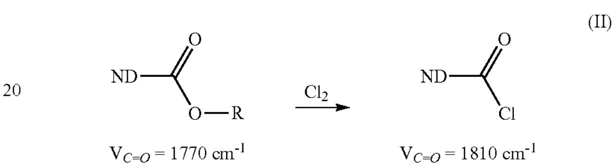

where R is H or a carbon-based group, such as $CH_3$. Chlorination may also remove carbon from the material due to the formation of volatile $CCl_4$.

In yet another embodiment of the invention, the chemically-reactive NDs are prepared by ammonia treatment of NDs for 1 hour at 850° C. This treatment may give rise to $NH_2$-containing groups on nanodiamonds. This treatment may also give rise to C—H, C═N and O—H containing surface functionalities.

Functionalization of the Surface of ND Particles

In one embodiment, the surface of the chemically-active nanodiamond particles included in the invention comprises carboxylic groups (—COOH). Chemically-active NDs with COOH surface groups have good dispersion stability in aqueous solutions at basic pH (Osswald et al., 2006, J. Am. Chem. Soc. 128(35): 11635-11642). Carboxylic groups on the surface of chemically-active nanodiamonds may be derivatized using methods known to those skilled in the arts.

As a non-limiting example, the carboxylic groups on the surface of chemically-active nanodiamonds may be reacted with an activating agent, such as, but not limited to, EDC (1-ethyl-3-(3-dimethylaminopropyl)carbodiimide), DCC (dicyclohexylcarbodiimide) or DIC (N,N'-diisopropylcarbodiimide), in an inert solvent such as, but not limited to, dichloromethane, tetrahydrofuran or dimethylformamide, and then reacted with a primary or secondary amine, yielding surface-functionalized NDs with immobilized amides.

In one embodiment, the amine is selected from the group consisting of octylamine, decylamine, undecylamine, dodecylamine, tridecylamine, tetradecylamine, pentadecylamine, hexadecylamine, heptadecylamine, dodecadecylamine, nonadecylamine and eicosylamine. In another embodiment, the amine is octadecylamine.

In another non-limiting example, the carboxylic groups on the surface of chemically-active NDs may be reacted with a chlorinating agent, such as, but not limited to, thionyl chloride, phosgene, diphosgene or triphosgene, in an inert solvent such as, but not limited to, dichloromethane, tetrahydrofuran or dimethylformamide, and then reacted with a primary or secondary amine, yielding surface-functionalized NDs with imnobilized amides.

In another embodiment, the surface of the chemically-active nanodiamond particles included in the invention comprises amino groups (—$NH_2$). Amino groups may be introduced on the surface of the chemically-active nanodiamonds by treating nanodiamonds with ammonia at high temperature. Amino groups may also be introduced on the surface of the chemically-active nanodiamonds by attaching bisamines to nanodiamonds containing surface carboxylic groups.

As a non-limiting example, the carboxylic groups on the surface of chemically-active nanodiamonds may be reacted with (i) an activating agent, such as, but not limited to, EDC (1-ethyl-3-(3-dimethylaminopropyl)carbodiimide), DCC (dicyclohexylcarbodiimide), or DIC (N,N'-diisopropylcarbodiimide), in an inert solvent such as, but not limited to, dichloromethane, tetrahydrofuran or dimethylformamide, or (ii) with a chlorinating agent, such as, but not limited to, thionyl chloride, phosgene, diphosgene or triphosgene, in an inert solvent such as, but not limited to, dichloromethane or tetrahydrofuran. The material may then be reacted with a bisamine, in an inert solvent such as, but not limited to, dichloromethane, tetrahydrofuran or dimethylformamide. In one aspect, the bisamine may have both amine groups in unprotected form, in which case the reaction yields an immobilized amide with a free amino group. In another aspect, the bisamine may have one unprotected amino group and one protected amino group, wherein the protective group may be, for example, t-butoxycarbonyl (Boc) or fluorenylmethoxycarbonyl (Fmoc). In this case the reaction yields an immobilized amide with a protected amino group. The protective group may be removed using conditions well known in the art, such as treatment with trifluoroacetic acid or hydrochloric acid in the case of the Boc protective group, or treatment with piperidine in dimethylformamide in the case of the Fmoc protective group. This procedure yields surface-functionalized NDs with amides containing free amines.

Formation of Bonds Between Surface-Functionalized ND Particles and Matrix

An important aspect of be considered in the preparation of nanodiamond-polymer composites included in the invention is the purity level of the starting ND particles. The content of non-diamond phase in as-produced or commercially available NDs may be as high as 75% wt. Purification of as-received or crude NDs using modification methods such as, but not limited to, air oxidation, hydrogenation, chlorination and ammonia treatment, and optional mechanical methods such as, but not limited to, treatment with acidic solutions, results in non-diamond carbon removal and generation of a material with the surface uniformly terminated by specific functional groups. In a non-limiting example, selective air oxidation of as-received ND in controlled conditions may increase the content of diamond phase from ~25 up to ~95% wt, and convert diverse surface functional groups of non-purified ND into C═O and COOH (Osswald et al., 2006, J. Am. Chem. Soc. 128(35):11635-11642).

In one embodiment, the nanocomposite material comprises 0.1% to 50% of surface-functionalized NDs. In another embodiment, the nanocomposite material comprises 0.5% to 50% of surface-functionalized NDs. In yet another embodiment, the nanocomposite material comprises 0.75% to 40% of surface-functionalized NDs. In yet another embodiment, the nanocomposite material comprises 1% to 30% of surface-functionalized NDs. In yet another embodiment, the nanocomposite material comprises 2% to 25% of surface-functionalized NDs. In yet another embodiment, the nanocomposite material comprises 3% to 20% of surface-functionalized NDs. In yet another embodiment, the nanocomposite material comprises 4% to 20% of surface-functionalized NDs. In yet another embodiment, the nanocomposite material comprises 5% to 15% of surface-functionalized NDs. In yet another embodiment, the nanocomposite material comprises 6% to 12% of surface-functionalized NDs. In yet another embodiment, the nanocomposite material comprises 8% to 12% of surface-functionalized NDs.

A strong interface between the surface-functionalized NDs included in the invention and the matrix must be present to ensure improved mechanical properties for the composite contemplated in the invention. One such strong interface may be obtained by forming strong covalent or non-covalent bonds between the surface-functionalized NDs and the matrix. In this case, for each polymer matrix, the surface-functionalized NDs would contain surface groups capable of forming strong hydrogen bonds or covalent bonds with the molecules of polymer matrix (FIG. 2*d*). Covalent bond formation between the purified surface-functionalized ND particles and polymer matrix will eventually lead to a "super-composite", a material that should fully realize the superior mechanical and thermal properties of ND nanodiamond.

In a non-limiting example, PLLA matrix and $NH_2$-terminated ND may be used to generate a covalently bound ND-matrix composite. PLLA matrix contains free terminal —COOH groups, which may be reacted with $NH_2$-terminated ND in the presence of a coupling reagent, such as, but not limited to, DCC (dicyclohexylearbodiimide), EDC (1-ethyl-3-(3-dimethylaminopropyl)carbodiimide), or DIC (N,N'-diisopropyl-carbodiimide), in an inert solvent such as, but not limited to, dichloromethane, tetrahydrofuran or dimethylformamide. This reaction results in amide bonds between the surface-functionalized ND particle and PLLA chains, as shown in reaction (III), (III)

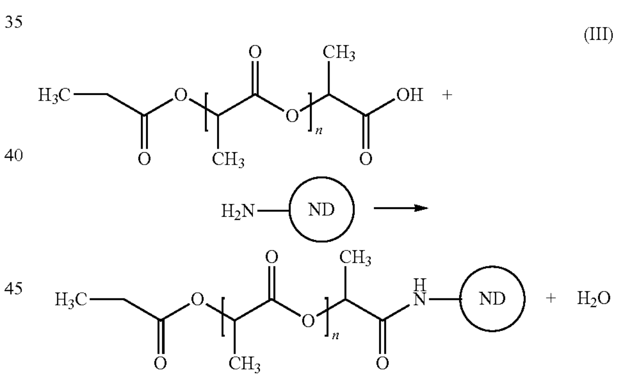

In another non-limiting example, PLLA matrix and —$NH_2$ or —COOH groups on the surface of functionalized ND powders may be used to form strong hydrogen bonds between the PLLA matrix and the ND particles.

In yet another non-limiting example, PLLA matrix and HO-terminated ND may be used to generate a covalently bound ND-matrix composite. PLLA matrix contains free terminal —COOH groups, which may be esterified with OH-terminated ND in the presence of a coupling agent such as DCC. Alternatively, the PLLA matrix may be treated with a chlorinating agent, such as thionyl chloride, to effect conversion of the carboxylic acid groups into acyl chloride groups. This material may then be reacted with HO-terminated ND to yield ester-linked ND-PLLA composites. Such chemical approaches may be extended to other polymers contemplated in the invention, depending on the specific functional groups that they contain.

Surgical Fixation Devices Containing Derivatized ND Particles

Surgical fixation devices are crucial for the treatment of bone-related problems. For example, more than 90,000 anterior cruciate ligament (ACL) reconstructive surgeries are performed annually worldwide (Bangash, "Trauma—An Engineering Analysis," Springer Berlin Heidelberg, 2007). This procedure involves replacing the torn ligament with new tissue (a graft), repairing and/or replacing the damaged ACL and dealing with knee instability, pain and recurrent swelling. For this, small holes are drilled in the bone, and the graft is passed through these holes. These grafts are then held in place and fixed using a wide range of surgical devices, such as plates, staples, anchors, interference screws and transverse pins. Good initial fixation of the properly positioned and tensioned graft is critical.

ACL procedures and other in bone/tissue structure fixation procedures would benefit from the development of a novel surgical fixation device that combines the property of supporting weight and providing support with the ability to eventually allow for regrowth of the bone material. The devices contemplated in the present invention address these uses.

The bioactive surgical fixation devices of the present invention are multi-functional. On one hand, they have the necessary stiffness and strength to be used in surgical procedures. On the other hand, they comprise a permeable medium that is able to deliver bioactive agents to the environment.

Nature is an excellent producer of similar multifunctional structures, e.g., wood, eggshell, wheat and rice, bone, skin, and others. These naturally porous materials all have a gradient cellular structure (GCS), with the porosity distributed in space so as to maximize the overall performance of the structure (Zhang et al., 2005, J. Zhejiang Univ. Sci. 6a(10):1095-1099; Kumar, 1993, Cell. Pol. 12(3):207-223; Suh, 2003, Macromol. Symp. 201:187-201; Gong et al., 2005, Int. Pol. Proc. 20(2):202-214; Kitimasak et al., 2003, Science Asia 29:95-98).

In bone, regions of dense "cortical" bone abut on regions of low-density "trabecular" bone. With pore sizes decreasing from the core to the exterior, bone is able to maintain a highly permeable core and yet provide outer wall structural integrity. In the avian eggshell, a GCS achieves desired mechanical performance and a necessary permeability. From inside to outside, the pore size varies from several 100 nm to a couple of microns (Zhang et al., 2005; Kitimasak et al., 2003), allowing for exchange of matter between the outside and inside of the eggshell while ensuring enough strength to prevent the shell from cracking caused by collision or impact. In summary, GCSs have the ability to integrate different, often contradictory, functions and achieve an optimized design.

The biomimetic devices of the invention present high structural integrity, with regulated variation of permeability throughout the device. Furthermore, variation of mechanical properties of the structure of the device of the invention may be controlled to match other materials at the interface of the device and the body.

Composite Surgical Fixation Devices

Surgical fixation devices have to be biocompatible, i.e., they may not cause an inflammatory or immune response in the body. However the current devices lack bioactive features. Specifically, these devices do not actively promote bone healing and regrowth, subsequently leaving voids in the tissue once the implanted surgical fixation device is removed (metal device) or fully degraded (biopolymer device).

The composite bioactive fixation device of the invention promotes bone healing and regrowth, based on the following engineering design criteria. The device of the invention is strong enough to withstand the mechanical stress during insertion and post-operative activity. Its degradation may be controllable to coincide with the rate of tissue growth. The fixation device of the invention may avoid the need for future implant removal operation due to adverse reactions or implant loosening.

The surgical fixation devices of the invention, such as, but not limited to, surgical screws, have two unique and critical components: (1) inclusion of nanodiamonds, which dramatically improve the mechanical properties of the biomaterials and serve as a biocompatible non-toxic scaffold to support growing cells; (2) porous shell structures for gradual release of hydrogels containing bone healing drugs (such as bisphosphonates, alendronate, ibandronate, risedronate, zoledronic acid, estrogen, raloxifene, calcitonin, or teriparatide), growth factors (such as bone morphogenetic protein 2 (BMP2), lactoferrin, Oxiplex™ (FzioMed, San Luis Obispo, Calif.) or bone growth factor rhGDF-5), antibiotics (such as vancomycin, clindamycin, tobramycin gentamycin, teicoplanin or synercid, or combinations thereof), anti-inflammatory drugs, bone cells, and bone stem cells, from a center core. The composite bioactive surgical devices of the invention also serve as scaffolds for osteoblasts to migrate into the screw, where they can proliferate/differentiate and finally form new bone tissue as the device degrades.

In one embodiment, the orthopedic surgical device is a sterile, single-use biodegradable and bioactive fixation system comprising a composite comprising NDs and poly-L-lactic-co-glycolic acid (PLGA) or PLLA.

In another embodiment, the device has embedded bioactive reagents such as bone healing drugs, growth factors, bone cells, bone stem cells, antibiotics, and/or anti-inflammatory drugs, to accelerate bone/tissue healing and recovery. Until now there has been no reported work on bioactive surgical fixation devices with gradient cellular wall/shell structure and nanodiamond reinforced polymers for bone tissue engineering. The device of the present invention is entirely composed of materials with a proven safety record and sufficient mechanical strength, and promotes faster bone growth than existing passive/inactive devices.

To fulfill the above design criteria, the surgical fixation device of the invention has two unique and critical components: (1) a core that is first used as the device driver interface and then, after the device insertion, is used as a reservoir to store syringe-injected hydrogel containing bioactive materials, and (2) an interconnective porous wall/shell, which allows local, controlled delivery of the biomaterials in question. The porous device also serves as a scaffold for osteoblasts to migrate into it, where they can proliferate/differentiate and finally form new bone tissue as the device degrades.

In one embodiment of the invention, the surgical fixation device is a screw, pin, rod, anchor or staple.

In another embodiment of the invention, the surgical fixation device is a screw.

Figure 5:
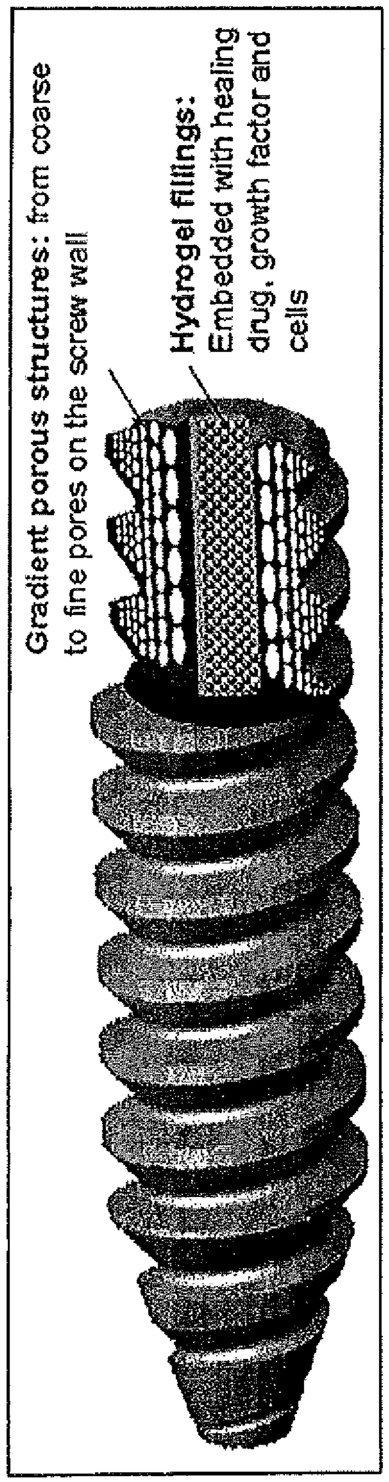
FIG. 5 is a schematic representation of a bioactive interference screw.

In yet another embodiment of the invention, a design for a bioactive interference screw is represented in FIG. 5. This screw may be used for ACL fixations, in a non-limiting example.

The screw possesses a rounded blunt posterior portion to prevent graft damage. The screw is tapered and without head so that it will not protrude out of the drilled hole. The tapered feature is specifically designed to provide maximum pull-out strength in ACL reconstruction. The screw is slightly more tapered at the tip to facilitate insertion taking into account the tight fit at this locale. In addition, these screws include full-length tapers so that the highest insertion torque is only realized once the screw is fully inserted, as to increase fixation and pullout strengths (Agrawal & Athanasiou, "A New Technique to Control the pH in the Vicinity of Biodegradable Implants," in Fifth World Biomaterials Congress, 1996, Toronto, Canada; De Groot, "Degradable ceramics," in "Biocompatibility of Clinical Implant Materials," D. F. Williams, Ed., CRC Press: Boca Raton, Fla., 1981, pages 199-222). A reduced thread pitch (the axial distance per screw turn) eases insertion by effectively reducing the screw "lead", which the screw uses to travel into the bone tunnel. This difference in "lead" reduces the stress within the screw as it is turned, ensuring that the screw is not subjected to forces beyond the material limits.

The design incorporates a tapered screw and a tapered driver, thus decreasing the insertion stress while maintaining fixation strength. This design minimizes driver stripping and screw breaking by optimizing stress distribution and force transfer. As a result, the tapered design reduces insertion torque, making insertion easier (Albee, Ann. Surg. 1920, 71(1):32-39; LeGeros et al., "Significance of the porosity and physical properties of calcium phosphate ceramics—Biodegradation bioresorption. A Task Group Report").

After the screws are inserted in the bone or tissue, the hollow core of the screws may additionally be filled with bioactive materials like growth factors, drugs and/or cells at the time of surgery in the operating room setting to stimulate bone growth. For maximum effectiveness, the bone adjacent to the screw and the bio-reagents in the core are connected with gradient cellular pores, creating a continuous system that accelerates bone regrowth upon insertion and filling the void upon degradation of the screw (FIG. 5).

Injection Molding of Controllable Porous Structures

Functional porous materials with controllable porous structures, to be used within the invention, may be prepared by injection molding an immiscible polymer blend, with spatially controlled thermal conditioning to adjust the phase size and its distribution. Controllable pore sizes and gradient porous structures may be obtained through control of the thermo-mechanical history of the blend during processing. This approach may be further developed for the production of a gradient porous biomaterial reinforced by nanodiamond and suitable for applications in implanted devices.

In one embodiment of the invention, polymers such as, but not limited to, PLA, PGA, or PLGA, are first melt-blended with a sacrificial, immiscible polymer (e.g., polystyrene) in a batch mixer to ensure the development of a fine blend structure with phase size of micrometers. The blend is then injection molded into the mold cavity for the bioactive device (which may be a screw, in a non-limiting example). While inside the mold, the blend is thermally conditioned with higher temperature at the core and lower temperature at the surface, resulting in the development of coarse phases at the core but fine phases at the surface. The interfacial surface tension between the two polymers causes coarsening of the phase structure at high-temperature regions. The gradient in phase size may be regulated by adjusting the thermal history. When the desired growth is reached, the mold is cooled and the screw is ejected. Finally, the sacrificial polymer in the screw is selectively dissolved to obtain desired porous structures.

Figure 6:
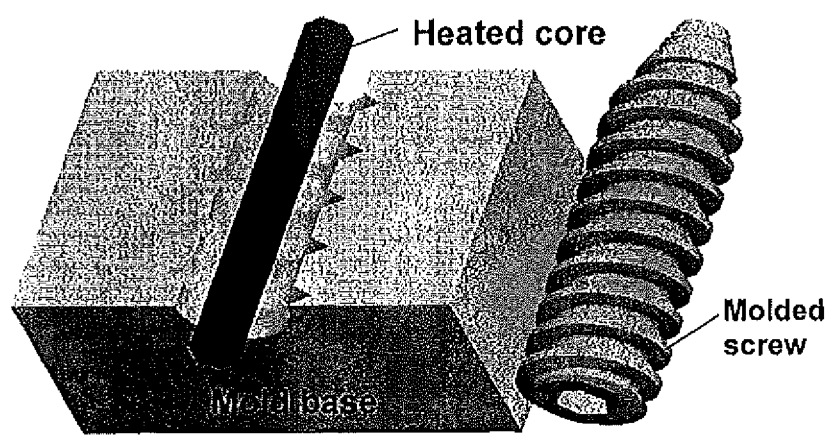
FIG. 6 is a schematic representation of a GCS (gradient cellular structure) mold with a heated core. The core temperature and the mold temperature may be controlled separately to create the desired thermal gradient.

To make a porous screw with a gradient, special handling is needed to create a suitable thermal boundary condition (FIG. 6). For this purpose, a thin cartridge heater is embedded in the hexagonal core to control the core temperature. A separate heating/cooling unit is employed in the mold base. This setup allows differential control of temperature from the surface to the core of the molding polymer. The different thermal history results in different degrees of coarsening in the phase structure, Particularly, it results in a coarser structure near the core and a finer one at the surface. A dwell time of a couple of minutes at an elevated temperature may result in a significant amount of structural coarsening. The desired structure may be approached through adjustment of the two temperatures, i.e., core and base temperatures.

Established rapid mold heating techniques (Yao & Kim, 2002, Pol. Eng. & Sci. 42(12):2471-2481; Yao & Kim, 2002, Pol.-Plast. Eng. Technol. 41(5):819-832; Yao et al., 2006, Pol. Eng. Sci. 46(7):938-945) may be used to rapidly heat the core and the mold, thus facilitating in situ control to yield the desired thermal history. In one embodiment, a normal filling process with a filling time on the order of 1 second is used, followed by a prolonged holding stage of several minutes, to thermally condition the phase structure. The actual mold and core temperatures and the hold time depend on the desired phase structure that needs to be grown. An inverse design (Kang et al., 1998, J. Therm. Stresses 21(2):141-155) approach may be employed for optimizing the thermal history and achieving the desired phase structure.

During selective dissolution, water and biocompatible solvents are used as a first choice. If other solvents are needed, the extraction is followed by careful flushing in water to remove all solvent residues. Particularly, a PLA/PCL system may be tested for its suitability. PCL is another biocompatible and biodegradable polymer, and it may be extracted with acetic acid. However, the two polymers have very different melting temperature, thus increasing the processing difficulty.

Other more polar polymers such as polystyrene (PS) may also be tested. In the case of PS, extraction starts with cyclohexanone, followed by an alcohol based solvent, and finally water. Alternatively, PLA (or PLGA) and PGA may be used to form a co-continuous phase morphology and subsequently the PGA phase may be degraded to form a porous PLA structure. This approach is based on the fact that PGA has a much higher degradation rate than PLA. Such a system is fully biocompatible since no solvent is involved. Another advantage of this method is that degradation of the PGA phase can be induced in vivo, allowing the use of a fully dense screw during insertion.

Mechanical and Biological Testing

The most frequent complication associated with biodegradable screws is screw breakage during insertion (Evans et al., 2002, J. Mat. Sci.-Mat. Med. 13(12):1143-1145; Barber et al., 2000, Biomaterials 21(24):2623-2629; Lee et al., 2005, Biomaterials 26(16):3249-3257). Material studies on the polymer-ND composite of the invention, including compression strength, tensile strength, Young's modulus, and pull-out strength, may shed light on the breakage problem. Compressive and tensile tests may be performed using a Tenius Olsen H25KT single column materials testing machine (Tenius Olsen, Horsham, Pa., USA). The maximum torque that may be applied to the screw may be determined with a torque meter. Pullout/pushout experiments may be performed using wood, and model bone, such as polyurethane foams and Sawbones, both of which are established tests that approximate the mechanical properties of real bone.

The resorption of the device of the invention in the body depends on the shape, size and site of implantation. The polymer resorbable composite should degrade in vivo in a manner consistent with healthy bone regeneration in bone augmentation and repair procedures. Without wishing to be bound by any theory, the fine particles of NDs are actively released together with fine particles of reduced-molecular weight PLGA, causing the structure to gradually degrade and shrink. This system leads to total repair of the bone once the device is completely disintegrated. This in vivo situation may be simulated in vitro by incubating and maintaining the bioactive screws under aseptic conditions in complete cell culture medium supplemented with 20% bovine serum. The decrease in molecular weight of the PLGA over time indicates the progression of degradation. The weight loss is measured over time and a comparison of cross-sectional images of the degrading bioactive device is made to determine the degradation rate of the device in vitro testing.

ND Composite Material Biotesting on Toxicity and Biocompatibility

Toxicity Screening

Toxicity of the materials included in the invention may be tested using extraction assays. Extracts are prepared by incubating surgical device material for up to 30 days in protein-containing culture medium. Human osteoblasts (ATCC, CRL-11372) are cultured in MEM culture medium supplemented with 10% fetal calf serum and antibiotics, with cell-free medium as negative controls. Potential toxicity-induced changes in cell morphology and detachment are monitored by fluorescent and scanning electron microscopy. Cell viability and proliferation are quantified over a 30-day period by using the Alamar blue assay (Mondrinos et al., 2006, Biomaterials 27(25):4399-4408; Nikolaychik et al., 1996, J. Biomater. Sci. Polym. Ed. 7:881-891).

Cell Attachment and Proliferation

Cell attachment and proliferation may be assessed by seeding composite disks with human osteoblasts. Composite materials are cast under aseptic conditions into 10-mm diameter 1.5-mm thick disks, to fit in 24-well plates. Following seeding, cell viability is assayed for up to 30 days using the Alamar Blue assay (Nikolaychik et al., 1996), Cell distribution in the disks is quantified after fixation and sectioning (10 μm) by light microscopy, following staining with hematoxylin and eosin, as well as by fluorescence microscopy of thicker sections (60 μm) after staining the nuclei and microfilaments with, respectively, Hoechst 33258 and rhodamine phalloidin (Li et al., 2006, Biomaterials 27(13):2705-2715; Li et al., 2005, Biomaterials 26(30):5999-6008).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention and should not be construed as an inflexible limitation on the scope of the invention. Moreover, all values that fall within these ranges, as well as the upper or lower limits of a range of values, are also contemplated by the present application. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

Nanodiamonds (NDs) of UD50, UD90 and UD98 grades were obtained from NanoBlox, Inc. (Boca Raton, Fla., USA). The number in the grade roughly corresponds to the diamond-to-graphite ratio in the material, as shown in FIG. 4.

Commercial and gas treated samples of NDs were characterized by Raman spectroscopy, using a Renishaw RM2000 UV Raman microspectrometer ($\lambda_{ex}$=325 nm) (Renishaw, Gloucestershire, UK); FTIR spectroscopy, using a Digilab Excalibur spectrometer (Digilab, Holliston, Mass.) with UMA 600 microscope; and High Resolution Transmission Electron Microscopy (HR-TEM) using a JEOL 2010F microscope (JEOL, Tokyo, JP).

Octadecylamine functionalized nanodiamond (ODA) powders were obtained from NanoBlox, Inc. (Boca Raton, Fla., USA).

PLLA was purchased from PURAC (Gorinchem, Netherlands).

All cell culture media and supplements were from Hyclone (Waltham, Mass.). Disposable tissue culture supplies were from Fisher Scientific (Pittsburgh, Pa.).

Gas Treatment:

Gas treatment has been performed in the apparatus described in the literature (Dash et al., 2004, Micropor. Mesopor. Mat. 72(1-3):203-208) using air, argon, $H_2$, $Cl_2$, and $NH_3$. Air was of "breathing quality" and other gases were of "high purity" or "ultra high purity" grades as supplied by Air Gas (USA).

The samples were treated according to the following protocol. ND powder (0.3-0.5 g) was placed into a quartz boat, weighed and inserted into a quartz tube positioned inside a tube furnace. The furnace tube was isolated from the atmosphere and purged with argon (30 ml/min) at room temperature for 1 hour to remove the ambient atmosphere. After purging, the flow of a reagent gas was started (30 ml/min), and heating was turned on. Upon achieving the desired temperature, the sample was held at this temperature under the reagent flow for a specified time. The furnace was switched off and the sample was allowed to cool to room temperature under the reagent gas flow. At the end of the experiment, the tube was purged with the inert gas for several hours to remove any traces of the reagent. Upon completion of the treatment, the quartz boat with the sample was removed from the tube and weighed again to determine weight change.

Nanocomposites Preparation:

PLLA (1 g) was dissolved in 10 ml of chloroform. A moderate amount of ND or ND-ODA calculated by weight percentage was weighed and put into 20-ml vial. After addition of 10 ml of chloroform, the mixture was placed under high power sonic for 30 min, then mixed with PLLA/chloroform solution immediately. The solvent in mixture was evaporated under stirring. The resulting thick film was used directly for further measurement.

Mechanical Tests:

Two kinds of ND powders were used: air-oxidized HCl-purified ND, and hydrophobic ND terminated with long aliphatic chains of octadecylamine (ND-ODA). Both powders were supplied by NanoBlox, Inc. The hardness tests were performed on Wilson Rockwell Hardness Tester (Instron Worldwide Headquarters, Norwood, Mass., USA). Six-ten point for each samples were measured.

In Vitro Biocompatibility:

In view of the long-term goal of generating scaffolds for bone tissue engineering, the U2OS osteosarcoma cell line was used for the study of cell attachment and proliferation on PLLA/ODA scaffolds. 7F2 cells were routinely maintained in alpha minimum essential medium (αMEM) with 10% FBS, 2.0 mM L-glutamine, 1.0 mM sodium pyruvate (VWR) in a 5% $CO_2$ incubator at 37° C. The scaffolds were incubated with 5% fibrin for 30 minutes to enhance cellular attachment. Then, the scaffolds were transferred to 24-well plates and seeded with a density of 50,000 cells/well. After 3 days, the samples were fixed in 10% neutral buffered formalin for 1 hour at room temperature and then left overnight in 1×PBS at 4° C. The samples were washed once with 1×PBS, and the cells were permeabilized for 15 minutes in 0.2% Triton-X 100 (Sigma-Aldrich, St. Louis, Mo.) in PBS (Cellgro, Manassas, Va.). Following a gentle wash in 1×PBS, the samples were incubated for 15 min in PBS containing 2 μg/mL Hoechst 33258 (bis-benzimide, Sigma-Aldrich) and 1 μg/mL rhodamine phalloidin (Phalloidin, TRITC-labeled, Sigma-Aldrich). Samples were visualized on a Leica DMRX microscope equipped with the appropriate fluorescence filters. Digital images were acquired using a Leica 300F camera.

Differential Scanning Calorimetry (DSC):

The thermal properties of the pure PLLA, 3 wt % ND-ODA/PLLA and wt % ND-ODA/PLLA composites were studied by DSC (TA Instruments DSC Q100, TA Instruments, New Castle, Del.), using 10 mg of various samples. All measurements were performed under nitrogen atmosphere at a heating rate of 10° C./min. All experiments were performed twice, yielding similar results.

Nuclear Magnetic Resonance (NMR):

The solid-state NMR experiments were carried out using a Bruker DMX500 (11.7 T) spectrometer operating at a Larmor frequency of 125.8 MHz for $^{13}$C. A tripletuned magic-angle spinning (MAS) probe was used. The 4 mm zirconia rotor containing roughly 70 mg of sample was spun at 12.5 kHz with automatic spinning control. Recycle delays of up to 64 s were used in direct polarization experiments while a recycle delay of 2 s was used in $^{1}$H-$^{13}$C cross polarization experiments. The $^{13}$C and $^{1}$H $\pi/2$ pulse lengths were 5 μs and TPPM decoupling of $^{1}$H was used during detection. Tetramethylsilane was used as an external chemical shift reference for $^{13}$C.

Dynamic Light Scattering (DLS):

ND-ODA particle size in PLLA/chloroform solution was measured at 20° C. in back scatter geometry using a Malvern Zetasizer Nano ZS (Malvern Instruments Ltd, UK) equipped with a 10 mW He—Ne laser (633 nm).

Transmission Electron Microscopy (TEM):

For Transmission Electron Microscopy (TEM) of the ND-ODA/PLLA films, the samples were sectioned at about 100 nm with a diamond knife using an Ultramicrotome Leica Ultracut EM UC6 at room temperature, and the sections were transferred from water to 200-mesh Cu TEM grid. Samples of ND-ODA suspension in chloroform were dropped on the Cu TEM grid with lacey carbon film and left to dry. TEM images were obtained with a JEOL JEM 2100 microscope at 200 kV. Photographs at different magnification were taken from several randomly selected spots on the grid to ensure that the results are representative.

Scanning Electron Microscopy (SEM):

To assess the morphology of 7F2 cells cultured on various ND-ODA/PLLA scaffolds by scanning electron microscopy (SEM), samples were dried with a critical point dryer (CPD, SPI CPD 7501, West Chester, Pa.) and characterized with an XL-30 Environmental SEM-FEG (Philips) using an acceleration voltage of 10 kV according to standard protocol (Li et al., 2005, Biomat. 26:5999-6008). A total of 3-4 images from independent preparations were evaluated.

Depth Sensing Indentation and Vickers Indentation:

Depth sensing indentation was performed using an MTS NanoIndenter XP (MTS, Eden Prairie, Minn.) with a 17 μm radius spherical tip. Indentation experiments were performed using continuous stiffness mode, according to the manufacturer's instructions. All tests were recorded at a constant strain rate of 0.05 $s^{-1}$ up to an indentation depth of 1,500 nm and the maximum load was held for 10 s to record creep. Unloading was performed to 10% of the maximum peak load followed by an additional 30 s hold segment for thermal drift correction. The modulus and hardness values were calculated after effective zero point correction as recommended by Kalidindi et al. (Acta Mater 2008, 56:3523-32) from the initial 50 nm elastic indentation segment. Stress-strain data were derived using the nanoindenter stiffness signal which was analyzed as described in literature (Kalidindi et al., 2008, Acta Mater 56:3523-32). Each sample was tested 10 times and one representative (near the middle of the set) curve of 10 was used for load-displacement and stress-strain analysis.

Vickers indentation tests were performed with a LECO M-400 Vickers hardness testing machine using a testing force of 2.94 N. The indents were photographed with an Olympus PMG3 light microscope.

X-Ray Diffraction (XRD):

XRD patterns were recorded using a Rigaku SmartLab X-ray diffractometer (Rigaku Corporation, Japan) with Cu Kα source. Samples were prepared by solvent casting on silicon wafer. The data were collected with a step size of 0.01° (2Θ) and count time 2 s per step between 10 and 30° (Kruger et al., 2005, Carbon 43:1722-30).

Real-Time Quantitative Polymerase Chain Reaction (RT-qPCR):

Total RNA was isolated with RNeasy Mini Kit (Qiagen, Valencia, Calif., USA). Genomic DNA was digested with RNase-free DNase set (Qiagen) according to the manufacturer's protocol. Following RNA isolation, the quality and quantity of the extracted RNA were analyzed with a Nanodrop 1000 (Thermo Fisher Scientific, Inc.). 0.6 μg of RNA was reverse transcribed with high capacity cDNA reverse transcription kit (Applied Biosystems, Foster City, Calif., USA). RT-qPCR was carried out using Taq-Man Universal PCR master mix (Applied Biosystems) and specific primers for osteocalcin (OCN, assay ID: Mm 03413826_mH) and alkaline phosphatase (ALP, assay ID: Mm 1187113_g1) on a Stratagene Mx3000P QPCR system (Agilent Technologies, Inc., USA). A comparative Ct method was used for analyzing the targeted gene expression levels, which were normalized to the Ct value of Taqman® murine housekeeping gene peptidylprolyl isomerase A (cyclophilin A, PPIA, assay ID: Mm 02342430_g1*). Relative fold of change was then calculated as $2^{-\Delta\Delta C_t}$. Each experiment was carried out independently three times and each sample was analyzed in duplicate. Statistical significance of the data was evaluated as described below.

Statistical Analysis:

All biological experiments were performed at least three times. Wherever possible data are expressed as mean f standard deviation (SD). Statistical analyses were performed using either ANOVA one-way analysis or ANOVA two-way analysis when applicable and significance was considered at $p<0.05$.

Example 1

Preparation and Characterization of Derivatized ND Particles 30 mg of ND, corresponding to compound 1 in reaction (IV) (UD90 grade, NanoBlox, Inc., USA), was purified by air oxidation and cleansed of metal impurities by boiling in 35% wt HCl for 24 hours, and then refluxed with 50 mL of $SOCl_2$ (Sigma Aldrich) and 1 mL of anhydrous N,N-dimethylformamide (DMF) (Sigma Aldrich), a well known catalyst for this reaction, at 70° C. for 24 h.

(IV)

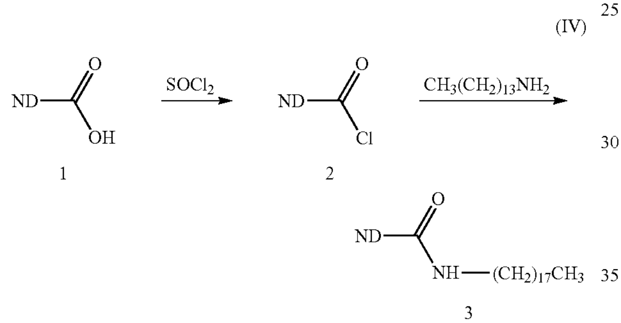

After removing the brown-colored liquid, compound 2 in reaction (IV) was washed with anhydrous tetrahydrofuran twice, and then dried at ambient temperature in a desiccator under vacuum. About 30 mg of the acyl chloride derivative 2 was stirred in a sealed flask with 1 g of octadecylamine, also known as ODA (Sigma Aldrich), at 90-100° C. for 96 hours. After cooling, excess ODA was removed by sonication with anhydrous methanol (Sigma Aldrich) 4-5 times. To remove adsorbed ODA, the material 3 in reaction (IV) was further purified by extraction with hot methanol in a Soxhlet apparatus. To ensure complete extraction, it was repeated 10 times with fresh methanol.

Figure 7:
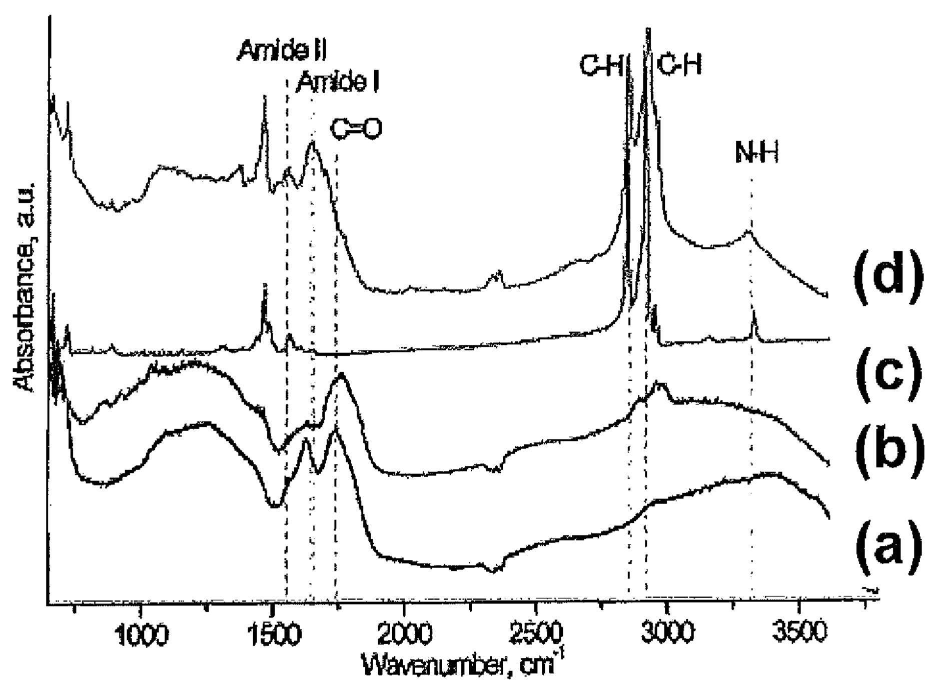
FIG. 7 is a graph depicting the FT-IR spectra of ND (line a), ND acyl chloride (line b), ODA (octadecylamine; line c), and ND-ODA (line d).

The sequence of reactions was monitored by FT-IR analysis of the products 1-3 (FIG. 7). C═O stretch vibrations in an acyl chloride derivative of ND were shifted to a higher frequency compared to the C═O band in ND, thus indicating the conversion of —COOH into —COCl (spectrum b in FIG. 7). Treatment of acyl chloride derivative with ODA resulted in formation of the amide III (spectrum d in FIG. 7). IR Amide I and Amide II bands at 1650 and 1550 $cm^{-1}$, respectively, in the spectrum of 3 (spectrum d in FIG. 7) provided a proof of covalent attachment of ODA through the amide bond formation, as opposed to physisorption of ODA. Other IR features of ND-ODA, such as strong C—H stretch vibrations at 2800-3000 $cm^{-1}$ characteristic of long hydrocarbon chains, and the N—H stretch of the amino group at 3300 $cm^{-1}$, could not be considered alone as proof of the amide 3 formation, because they might appear in the spectrum simply as a result of ODA physisorption.

Figure 8:
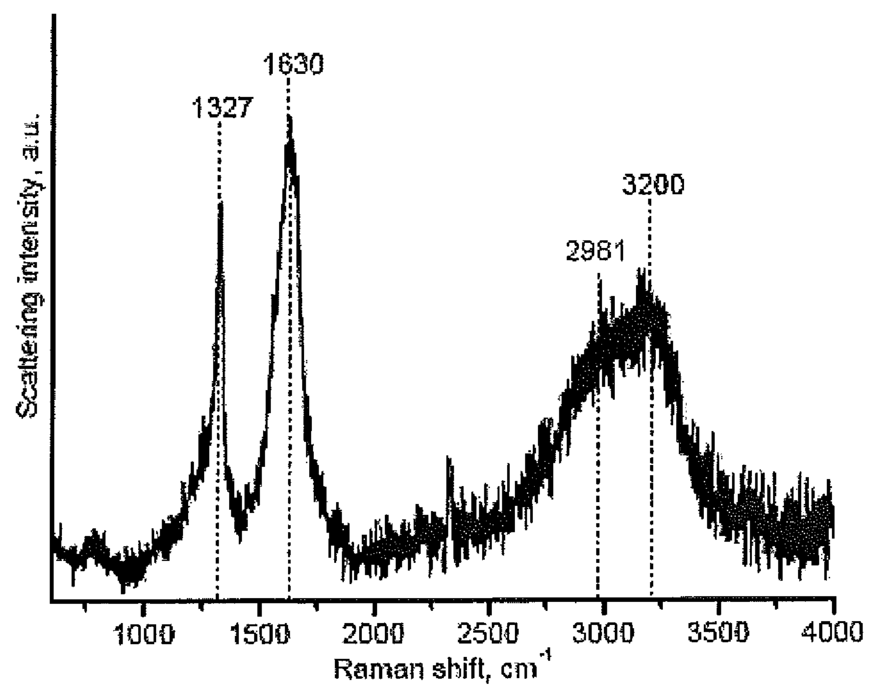
FIG. 8 is a graph depicting the UV Raman spectrum of ND-ODA powder.

A UV Raman spectrum of ND-ODA 3 (FIG. 8) revealed typical features of nanodiamond: a broad and downshifted peak of diamond at 1327 $cm^{-1}$ and a broad intense peak at 1630 $cm^{-1}$. The unresolved peaks of C—H (at ~2980 $cm^{-1}$) and N—H (at ~3200 $cm^{-1}$) were also present in agreement with the structure 3. These latter Raman peaks overlapped with the second-order spectrum of $sp^2$ carbon in ND.

Figure 18:
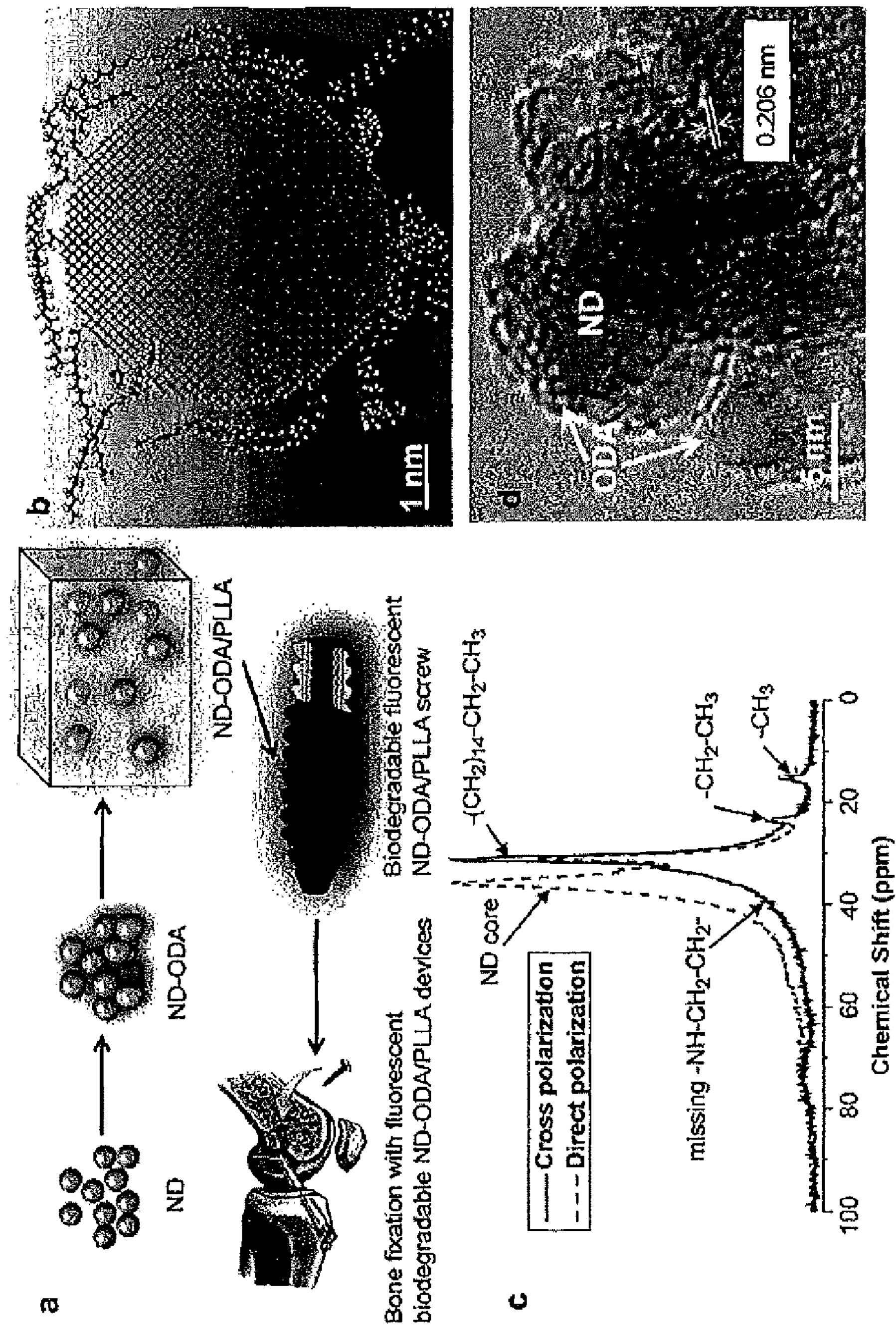
FIG. 18, comprising

A model of a single ND-ODA particle is shown in FIG. 18*b*. Analysis of ND-ODA by $^{13}C$ NMR provided evidence for the covalent linking of the ODA chains to the surface of ND (FIG. 18*c*). In particular, signals of first, second, and perhaps additional carbon atoms of ODA in $^{1}H$ to $^{13}C$ cross polarization spectra of ND-ODA were missing due to interactions of the atoms near the amine end of ODA with the large ND particle. Similarly, the missing signals of carbon atoms nearest to the amide bond have been reported before for ODA covalently linked to carbon nano-onions (Rettenbacher et al., 2006, Chem, Eur. J. 12:376-87) and multi-walled carbon nanotubes (Xu et al., 2003, Chem. Phys. Lett. 375:598-604).

The disappearance was due to a combination of broadening effects including the increased steric hindrance, variations in local structure, and the presence of paramagnetic species. These effects suggested a covalent linkage between the ND and ODA. As a result of this covalent linkage, ND-ODA is hydrophobic and strongly fluorescent in contrast to as-received non-modified ND. FIG. 18*d* shows High Resolution Transmission Electron Microscopy (TEM) image of ND-ODA particles with lattice fringes at 0.206 nm ([111] planes of diamond) surrounded by, presumably, the ODA chains.

Purified ND-ODA powder 3 was used in subsequent studies.

Example 2

Dispersion of Non-Functionalized and Surface-Functionalized NDs in PLLA

Due to the long hydrocarbon chains linked to its surface, the ND-ODA could be easily dispersed in hydrophobic solvents such as benzene, toluene, chloroform, and dichloromethane. At the same time, it was immiscible with water and poorly miscible with hydrophilic organic solvents such as DMF, ethanol, methanol, and acetone.

Figure 9:
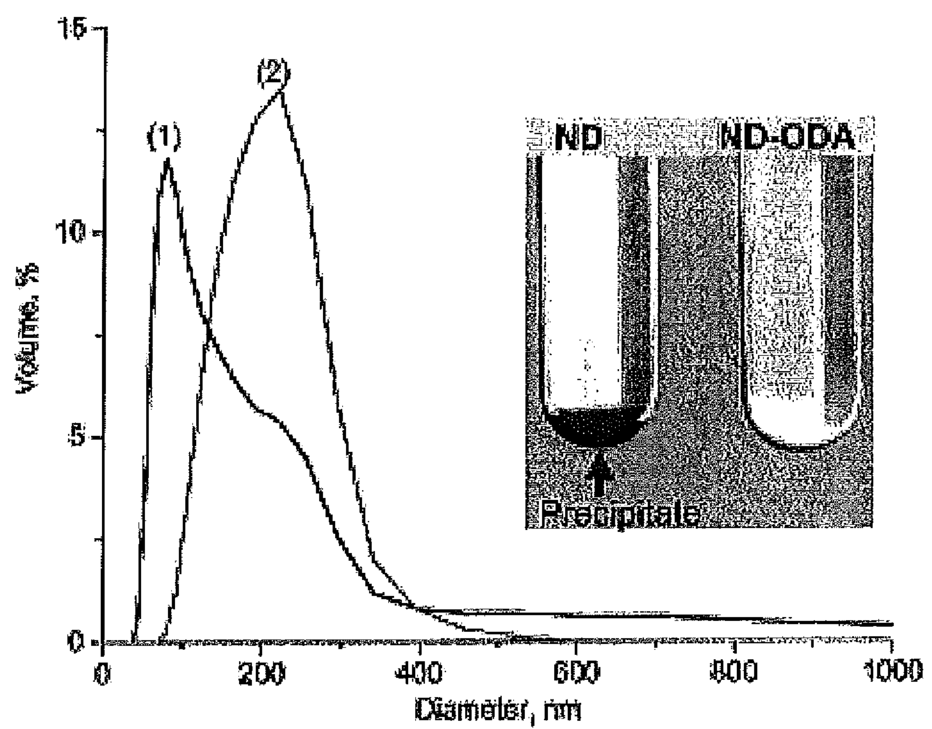
FIG. 9 is a graph demonstrating the particle size of ND-ODA in toluene (line 1) and chloroform (line 2). The inset is a photograph of 0.01% wt suspensions of ND and ND-ODA in toluene.

After being dispersed in toluene with ultrasonication, NDs completely precipitated within 1 hour (FIG. 9). On the other hand, ND-ODA without any sonication or other means formed a clear, stable pale yellowish (or brown at high concentrations) colloidal solution, which showed no visible precipitation over a week. Particle size measurements revealed 100-300 nm ND-ODA agglomerates in toluene and chloroform (FIG. 9) in contrast to 5,000-9,000 nm agglomerates formed in DMF. No sonication, surfactants, or other special means of dispersing were necessary for ND-ODA. The solubility of ND-ODA, based on gravimetric estimations, was ~4 g/L in dichloromethane and ~3 g/L in toluene.

To test the dispersion of ND in PLLA, mixtures of 6% wt ND and 6% wt ND-ODA in PLLA/chloroform were prepared. The ODA/PLLA mixture was centrifuged at 500 rmp for 30 min and then kept still for 1 week without any stirring. During this time, there was no phase separation observed in the mixture (FIG. 10*b*).

Figure 10:
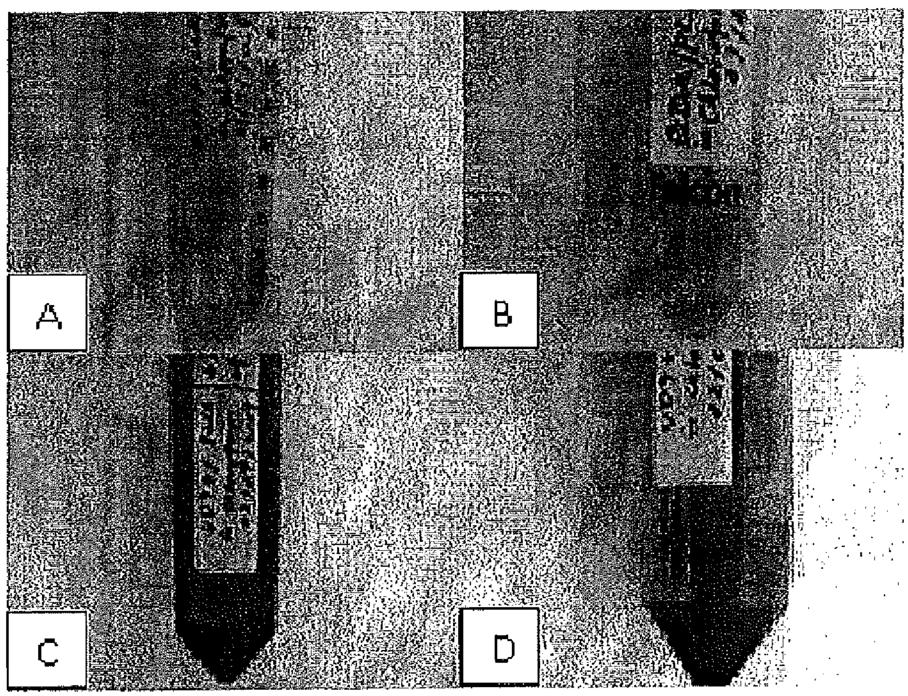
FIG. 10, comprising

However, the suspension of ND/PLLA prepared in the same way in chloroform precipitated within 1 day of standing without any centrifugation (FIG. 10*d*). This result suggested that ND-ODA has better dispersion in chloroform/PLLA system than ND. This result also suggests an interaction between ODA and PLLA.

Figure 19:
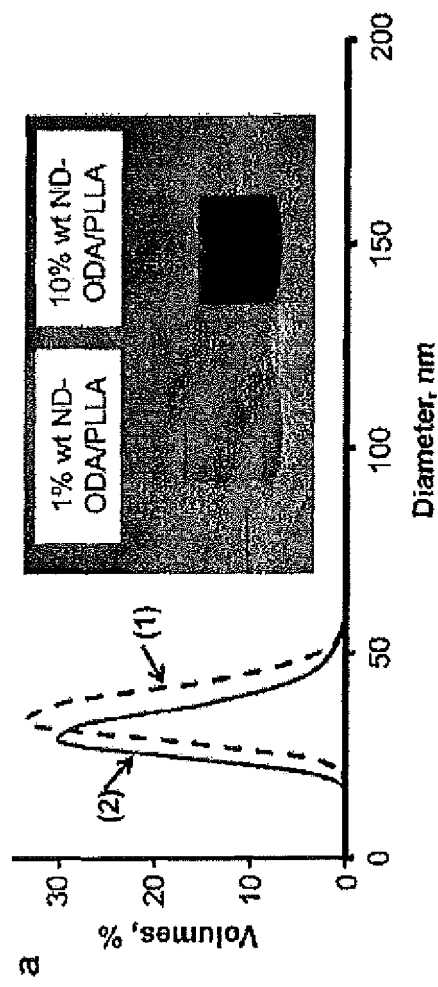
FIG. 19, comprising
Figure 19:
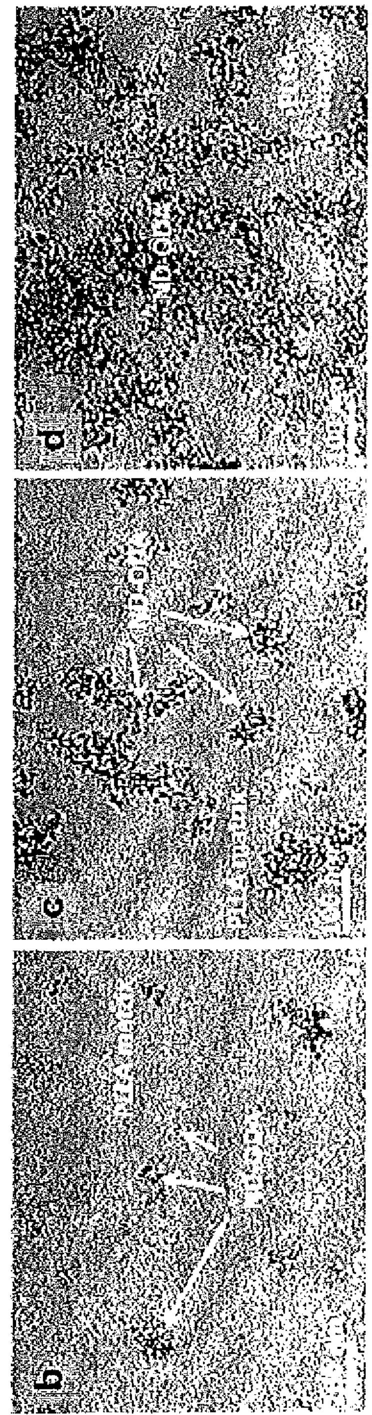

The hydrodynamic diameter of ND-ODA in PLLA-chloroform solutions determined by Dynamic Light Scattering (DLS) was narrowly distributed around maxima at 33±3 nm for 1% wt NDODA/PLLA and 28±2 inn for 10% wt ND-ODA/PLLA, respectively (FIG. 19*a*). Given the 5 nm diameter of primary ND particles, one could conclude that the sizes measured by DLS correspond to aggregates of >5 particles. However, the length of an ODA chain linked to ND appears to be about a half of the diameter of an ND (2.5 nm, FIG. 18*b*), i.e. the diameter of ND-ODA primary particles could be as much as twice larger than 5 nm. Thus the hydrodynamic diameters measured by DLS are likely those of small ND-ODA aggregates composed of just a few particles.

The dispersion of ND-ODA in a solid PLLA matrix was observed by TEM of ultrathin sectioned samples (100 nm thick) containing 1, 3, and 10% wt of ND-ODA. At 1% wt concentration, low resolution TEM images (FIG. 19*b*) suggested small ND-ODA agglomerates, tens of nanometers in size. No further increase in the agglomerates' size or density was observed at higher concentrations (FIGS. 19*c* and 19*d*), Instead, when the concentration was increased, interconnected particle chains were formed (FIG. 19*d*). Thus, DLS measurements and TEM micrographs converge to a conclusion that there is no strong agglomeration or phase separation of ND-ODA and PLLA in the composites up to, at least, 10% wt of ND-ODA.

Example 3

Mechanical Tests in PLLA

Results were produced on PLLA with two kinds of ND powders: air-oxidized HCl-purified ND, and hydrophobic ND terminated with long aliphatic chains of octadecylamine (ODA) (Mochalin et al., "High temperature functionalization and surface modification of nanodiamond powders," In "Materials Research Society Symposium Proceedings Boston," MA, USA, 2007, Vol. 1039, 1039-P11-03). The hardness tests were performed on a Wilson Rockwell Hardness Tester (Instron Worldwide Headquarters, Norwood, Mass.).

Figure 11:
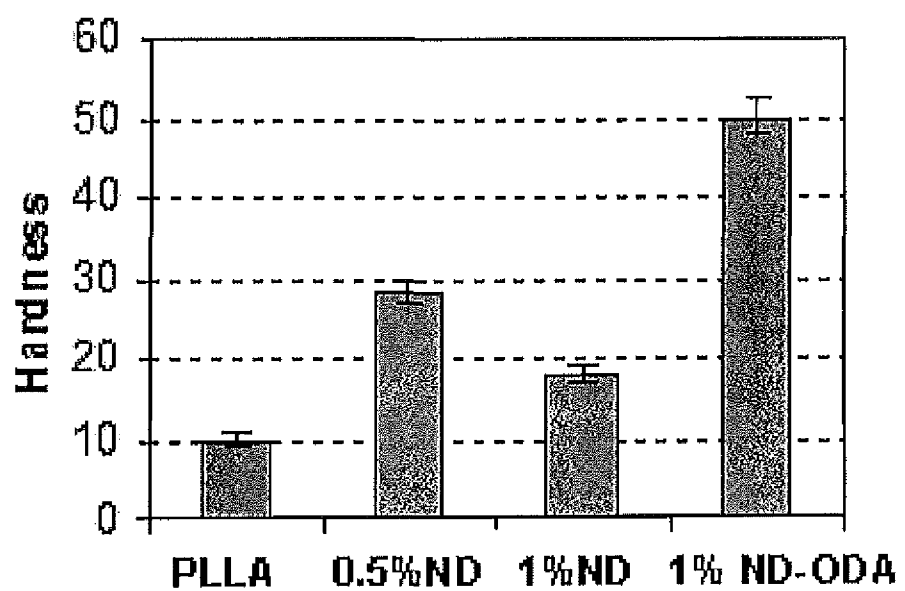
FIG. 11 is a bar graph comparing the hardness of PLLA-ND with different content of NDs and ND-ODA (% wt).

FIG. 11 depicts the hardness of the composites produced with ND and ND-ODA. The hardness increased about 2 times when adding 0.5% wt. of air oxidized HCl purified ND into PLLA. However, it decreased when adding more air oxidized HCl purified ND (1% wt) into the biopolymer. This behavior is similar to results of d'Almeida et al. (J. Reinf. Plast. Comp., 2007, 26(3), 321-330) and is due to a poor dispersion of the purified but non-functionalized ND in the polymer.

In contrast, addition of 1% wt of ND-ODA (functionalized ND) increased the hardness of the composite dramatically (>4 times). These results provide strong evidence of improvement in mechanical properties produced with the use of functionalized ND composites within biocompatible and biodegradable composites.

Example 4

Mechanical Tests in PA-11 (Polyamide-11)

Figure 12:
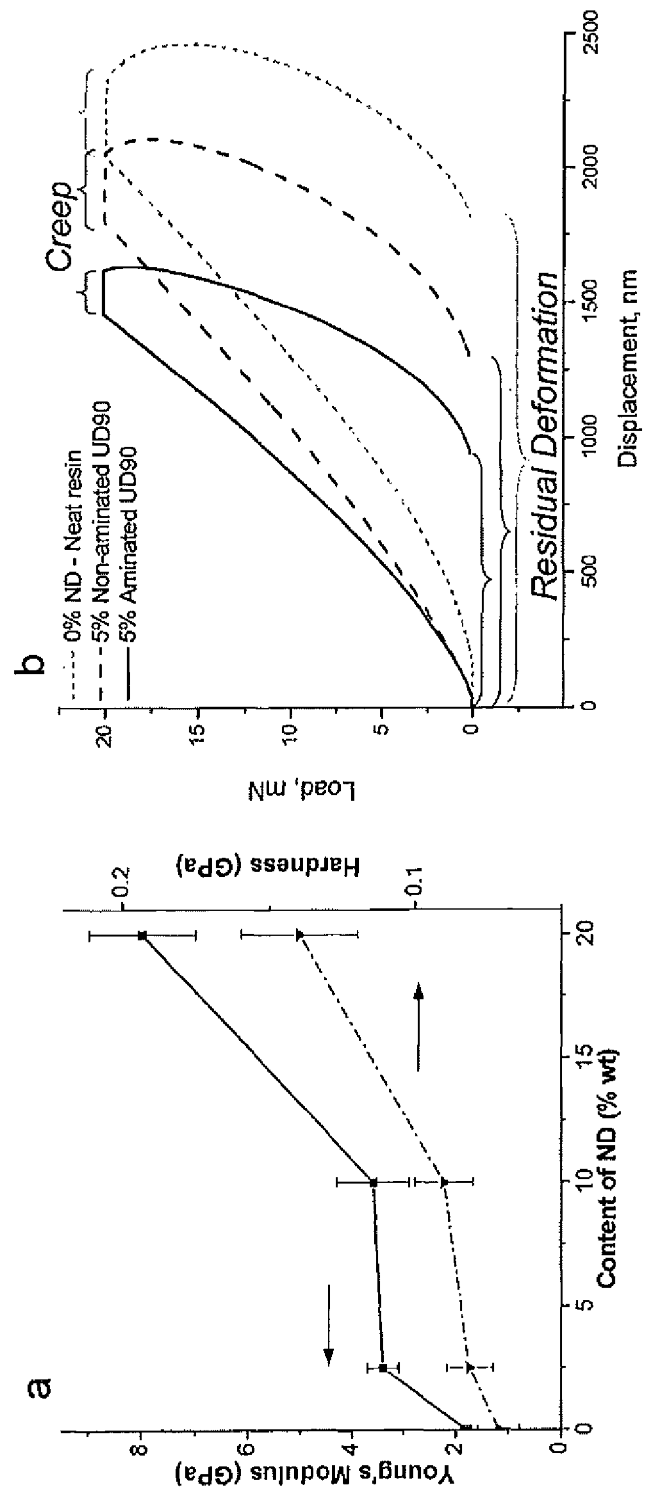
FIG. 12, comprising

Compositions of PA-11/ND with up to 20% wt of ND were produced in the form of nanofibers and thin films from oxidized and HCl purified ND (UD90-grade) supplied by NanoBlox. Addition of ND significantly improved mechanical properties of PA-11 films, raising their Young's modulus by a factor of 4 and more than doubling the hardness (FIG. 12*a*).

Example 5

Epoxy-ND Composites

Two kinds of ND powders were used: air oxidized HCl purified ND, and a special $NH_2$-terminated nanodiamond, produced by selective conversion of the ND surface COOH groups into amino groups. $NH_2$-terminated ND was expected to react with epoxy resin and form strong covalent ND/polymer interface, resulting in further improvement in mechanical properties of the composites.

Compared to the neat epoxy samples (0% wt of ND), the samples with 5% wt of ND demonstrate higher Young's modulus and hardness (Table 1). Especially notable is the about two-fold decrease in creep rate (FIG. 12*b*) and the significant increase in hardness that were only observed for composites with aminated ND. These preliminary results provided an indication of improvement in mechanical properties of the composites with ND covalently bonded to the polymer chains.

TABLE 1

Young's modulus and hardness of epoxy with and without ND reinforcement.

| Sample | Young's Modulus, GPa | Hardness, GPa |
|---|---|---|
| 0% wt. ND | 2.7 | 0.17 |
| 5% wt. non-aminated ND | 5 | 0.18 |
| 5% wt. aminated ND | 6.3 | 0.23 |

Figure 20:
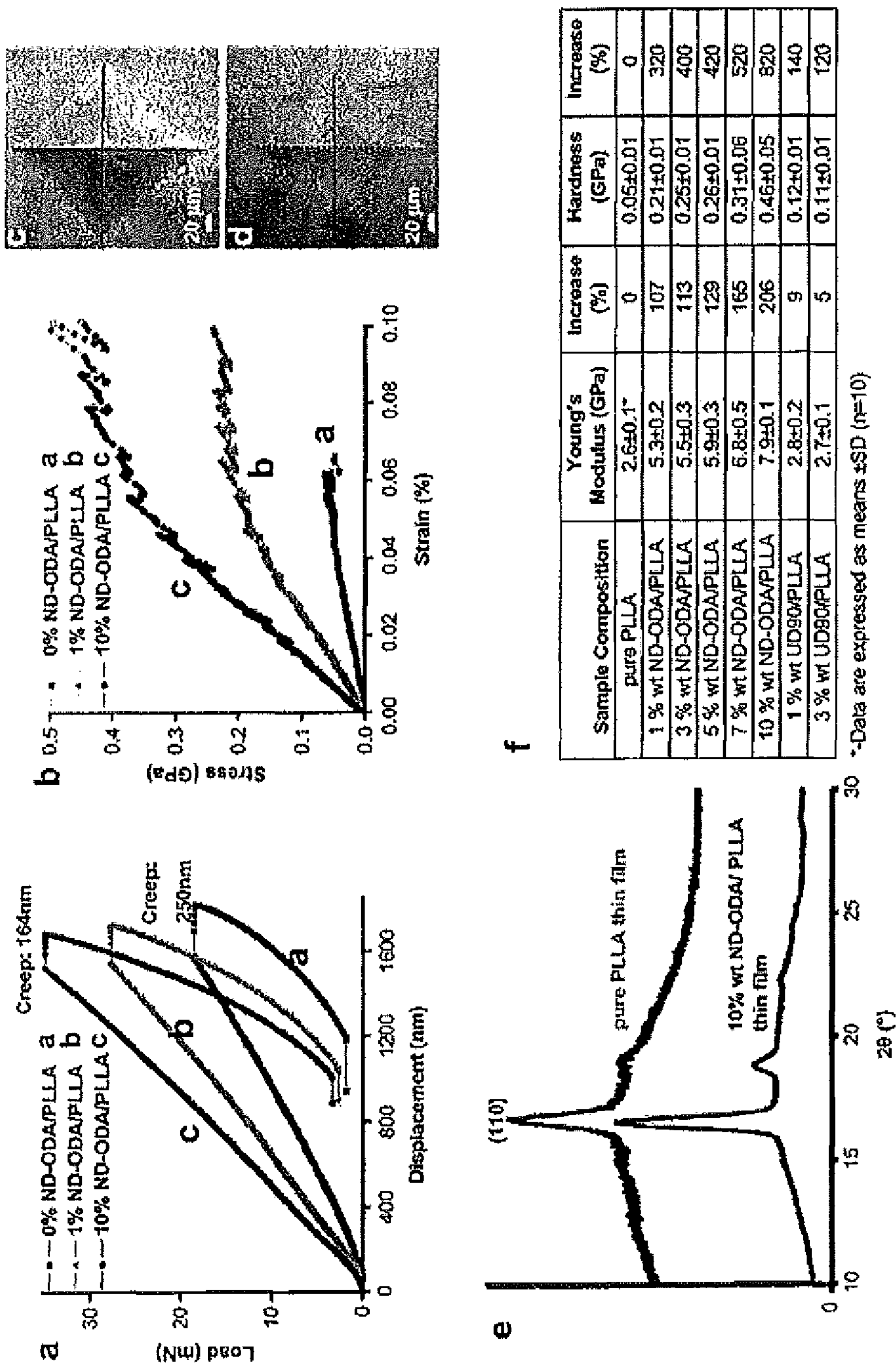
FIG. 20, comprising

Shown in FIG. 20*a* are load-displacement curves for ND-ODA/PLLA obtained by nanoindentation, Stress-strain curves derived from these data are illustrated in FIG. 20*b*. Young's modulus and hardness of the composites, calculated after effective zero point correction (Kalidindi et al., 2008, Acta Mater. 56:3523-32), are presented in FIG. 20*f*. The experimental Young's modulus of the PLLA thin film was 2.6±0.1 GPa, which agrees well with the value of 2.05 GPa reported for the amorphous PLLA film by Martin et al. (Polymer 2001, 42:6209-19). The measured hardness of the PLLA film was 0.05±0.01 GPa. The modulus and hardness of our PLLA thin films were lower than those previously reported for PLLA samples produced by injection molding (Young's modulus 4.6 GPa and hardness 0.23 GPa) (Wright-Charlesworth et al., 2005, J. Biomed. Mater. Res A 74A:388-96). This may be explained by different crystallinity of the present PLLA samples produced by solution casting (more amorphous PLLA) and those reported in literature, which were subjected to elevated temperature and mechanical drawing during the injection molding process (more crystalline PLLA).

Introduction of ND-ODA into the PLLA matrix resulted in an increase in the mechanical properties at all concentrations studied (FIG. 20*f*). Supplementation with 1% wt of ND-ODA yielded a 207% higher Young's modulus and 420% higher Meyer's hardness. Further increase in ND-ODA content produced a marked reduction of 35% in creep (FIG. 20*a*) and led to a further, though less pronounced increases in hardness and modulus with smaller changes at higher ND-ODA loads. Similar effects were recently reported for ND/poly(vinyl alcohol) composites (Maitra et al., 2009, Solid State Commun. 149:1693-97) where the most dramatic increase in Young's modulus and hardness occurred at very low concentrations of ND (0-0.2% wt). Thus the present experimental results suggest that even at low ND content a significant improvement in mechanical properties of the polymer matrix may be achieved given the ND has good affinity and is uniformly distributed in the matrix. In the case of PLLA-based composites strongly hydrophobic filler, such as ND-ODA, are preferred, since this material has good affinity to PLLA and may be well dispersed in hydrophobic solvents (such as chloroform) that are used in solution casting of PLLA. The crucial role of the hydrophobicity of ND-ODA is emphasized by a comparison with the results for as-received hydrophilic ND terminated with oxygen containing functional groups (Osswald et al. 2006, J. Am. chem. Soc. 11635-42) (FIG. 20*f*, last two rows). In contrast to ND-ODA, the additions of 1 and 3% wt of the asr-eceived ND (UD90) did not produce any significant changes in Young's modulus and led to a much smaller increase in hardness. Interestingly, when non-modified diamond particles with no affinity to the matrix were added, sometimes even a concentration-dependent decrease in mechanical properties of polymer matrix was observed, which may be due to poor dispersion and poor adhesion between the diamond particles and the matrix (d'Almeida et al., 2007, J. Reinforc. Plast. Compos. 26:321-30).

Vickers indentation provided further evidence for a dramatic improvement in the elastic recovery of the ND-ODA/PLLA samples. In contrast to a clear Vickers imprint in pure PLLA (FIG. 20*c*), an imprint left in a 10% wt ND-ODA/PLLA was hardly visible (FIG. 20*d*), suggesting almost complete elastic recovery in the latter case. To explain the observed improvement in mechanical properties of PLLA upon addition of ND-ODA, two possible mechanisms could be considered. First, the improvement could be due to intrinsic high hardness and Young's modulus of the nanodiamond. Second, the nanofiller could increase the crystallinity of the polymer matrix which also translates into higher hardness and Young's modulus of the composite. To understand how ND-ODA influences the crystallinity of PLLA, X-Ray Diffraction (XRD) patterns of pure PLLA and 10% wt ND-ODA/PLLA thin films were recorded, both produced by solution casting. In order to compare the crystallinity, the XRD patterns of the films were normalized to the maximum intensity without background correction (FIG. 20*e*). The diffraction from the crystalline regions that were present even in amorphous PLLA had several characteristic maxima, the two strongest are at 2θ of ~17° and ~19° corresponding to a typical PLLA pseudoorthorhombic α structure (Hoogsteen et al., 1990, Macromol. 23:634-42). These peaks were present in XRD pattern of the neat PLLA film (FIG. 20*e*) on top of a well-pronounced amorphous halo from 100 to 200. The XRD pattern of 10% wt ND-ODA/PLLA film also showed clear Bragg peaks of PLLA crystalline phase at 2Θ of ~17° and ~19° (corresponding to (110) crystal reflection; Wang et al., 2001, Polymer 42:8965-73), with a significantly suppressed amorphous halo, which was indicative of increased crystallinity of the composite compared to the neat PLLA film. The peaks at ~17° were fit with Lorentz functions. FWHM (Full Width at Half Maximum) values obtained from the peak fitting are 0.563±0.007° for neat PLLA and 0.474±0.0070 for 10% wt ND-ODA/PLLA. The narrower peak of 10% wt ND-ODA/PLLA provided further evidence of the higher crystallinity of ND-ODA/PLLA. Thus, well-dispersed ND-ODA particles increased crystallinity of the PLLA matrix, which in turn led to the enhanced hardness and Young's modulus of the composite.

Example 6

Biocompatibility & Cellular Proliferation

PLLA is amongst the most commonly used synthetic biodegradable polymers, with an extensive U.S. FDA approval history. When PLLA is combined with nanodiamonds to generate composites, the properties of the resulting material may differ from the original properties of PLLA.

Figure 13:
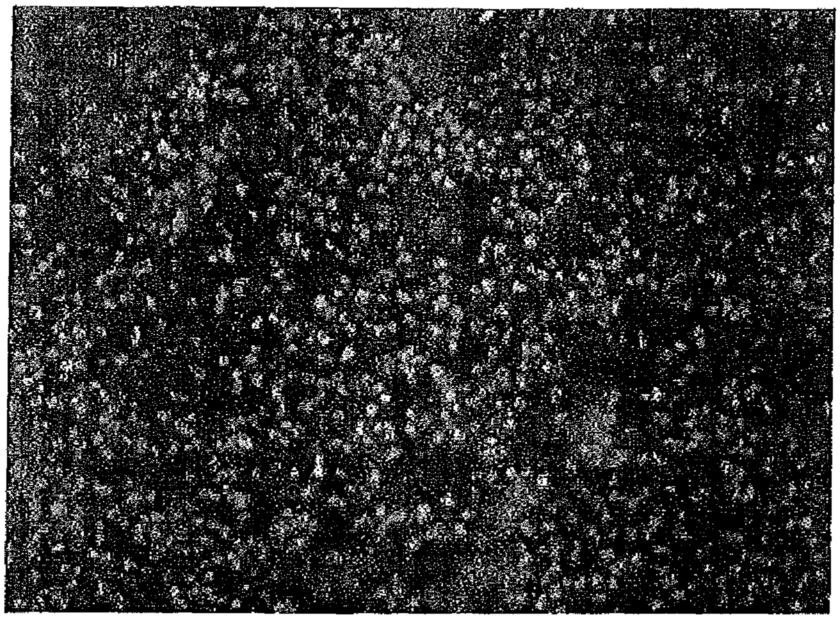
FIG. 13, comprising

In order to assess the biocompatibility of ND-ODA/PLLA composites, osteosarcoma cells (U2OS cells) were seeded on pure PLLA and ND-ODA/PLLA (0.5% wt of ND-ODA) scaffolds, FIG. 13 shows the cell morphology after 3 days cell culture, demonstrating that ND-ODA/PLLA scaffold supported cell attachment. The cell attachment on ND-ODA/PLLA scaffold was as good as on pure PLLA scaffold, as visualized by nuclear staining with bisbenbenzimide (Hoechst 33258). This result indicated that the ND-ODA/PLLA composites are biocompatible and may be used for tissue engineering.

Figure 24:
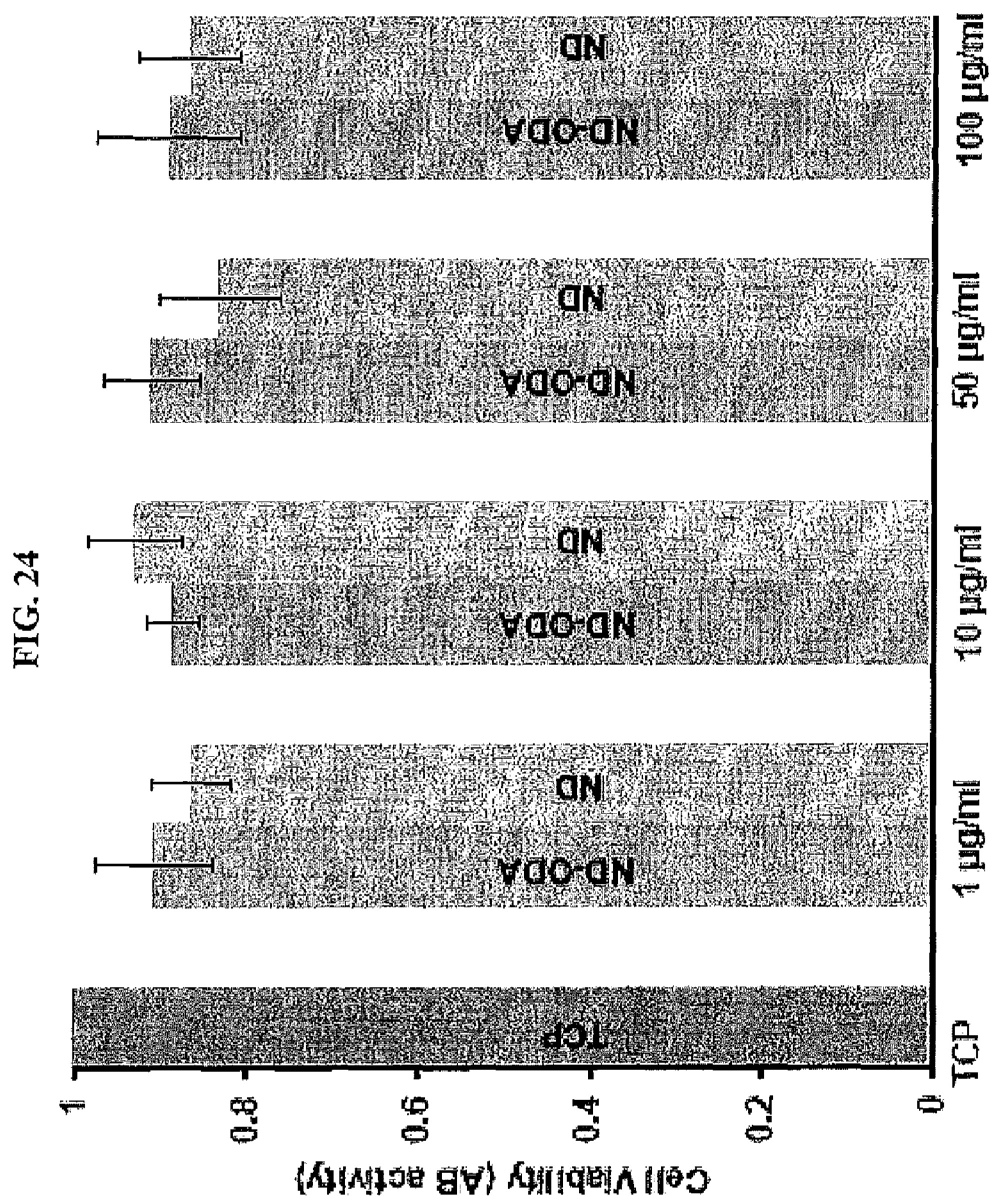
FIG. 24 is a bar graph illustrating a cytotoxicity test for ND and ND-ODA. Cell viability assay (alamarBlue™ (AB) based) of 7F2 mouse osteoblasts grown on tissue culture plastic (TCP) in the presence of ND or ND-ODA. Error bars represent the standard deviation for each sample (n=6).

ND is known to be less cytotoxic than carbon black or any other known carbon nanomaterial (Schrand et al., 2009, "From manufacturing to medical applications." New York: Springer; 2099, p. 159-87). However, cytotoxicity may be affected by ND functionalization. In order to determine the toxicity and biocompatibility of ND-ODA, the effects of native and functionalized ND on murine 7F2 osteoblast cells, using the fluorescent alamarBlue™ (AB) assay, were tested. The exposure of the cells to either ND or ND-ODA in concentrations up to 100 μg/ml resulted in a slight (though statistically not significant) reduction in cell viability compared to control, i.e. untreated cells grown on tissue culturetreated polystyrene, TCP (FIG. 24). This result suggested that, in the presence of ND or ND-ODA, the cells survived and grew essentially normally. ND with diameters 2-100 nm at concentrations up to 1000 μg/ml are nontoxic for different cell types, such as neuroblastoma, kidney, and epithelial cells (Schrand et al., 2007, J. Phys. Chem. B 111:2-7; Chao et al., 2007, Biophys. J. 93:2199-2208). The present results suggest that NDs with ODA attached are nontoxic for 7F2 osteoblasts.

Figure 21:
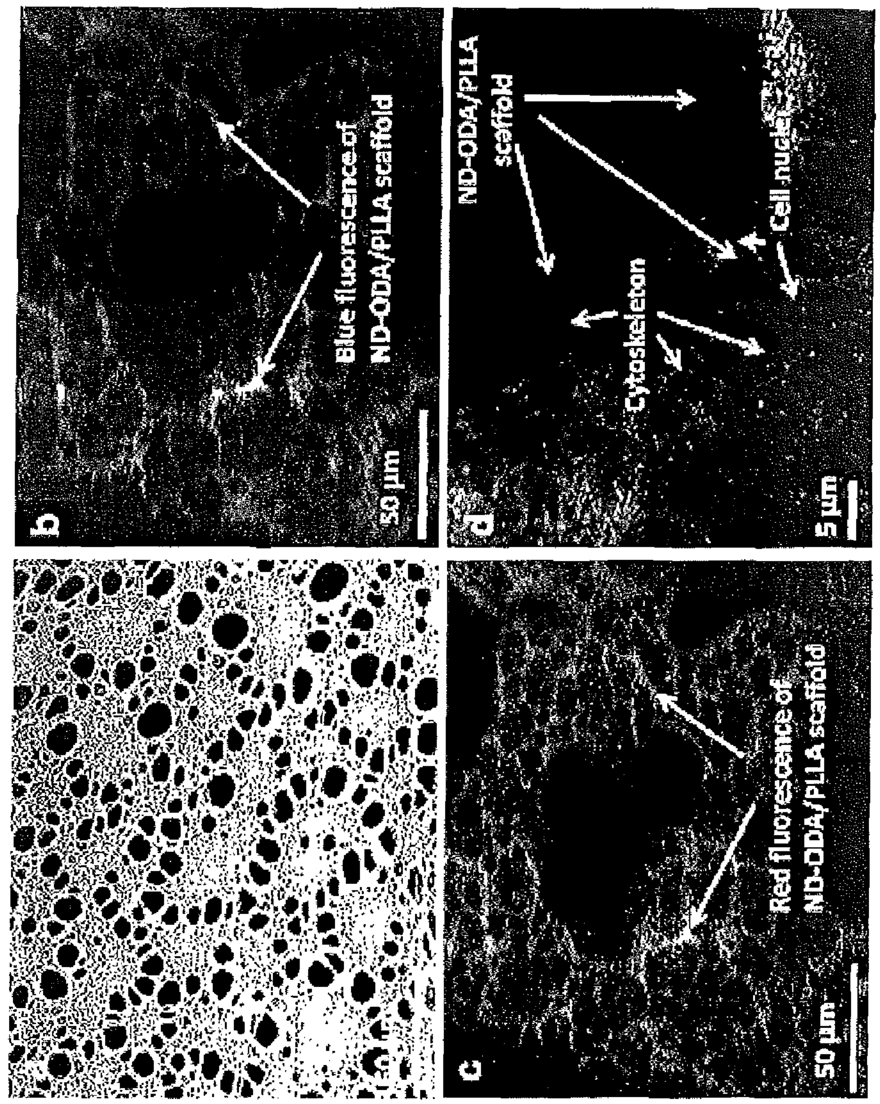
FIG. 21, comprising

In addition to ND and ND-ODA powders, biocompatibility of ND-ODA/PLLA composites was also tested. In these studies, osteoblasts were seeded on scaffolds made of PLLA containing 0-10% wt of ND-ODA and, on glass and TCP substrates as controls. The osteoblasts proliferated similarly on all substrates during the 6 days of culturing with only small, statistically insignificant differences (FIG. 25). FIG. 21 illustrates a typical SEM image of the porous structure of the 10% wt ND-ODA/PLLA thin film produced through solution casting. Porous structure formed as a result of solvent evaporation facilitated cell attachment and growth. Due to the presence of ND-ODA in the PLLA matrix, the film showed blue and red fluorescence under excitation at 360 and 555 nm (seen as light areas in the figures; FIGS. 21*b* and 21*c*), which coincide with the porous structure observed under SEM. The clear fluorescence of the 10% wt ND-ODA/PLLA scaffold in background of the 7F2 osteoblasts after 3 days post-seeding (FIG. 21*d*) indicated the possibility to monitor the composite degradation in situ.

Figure 22:
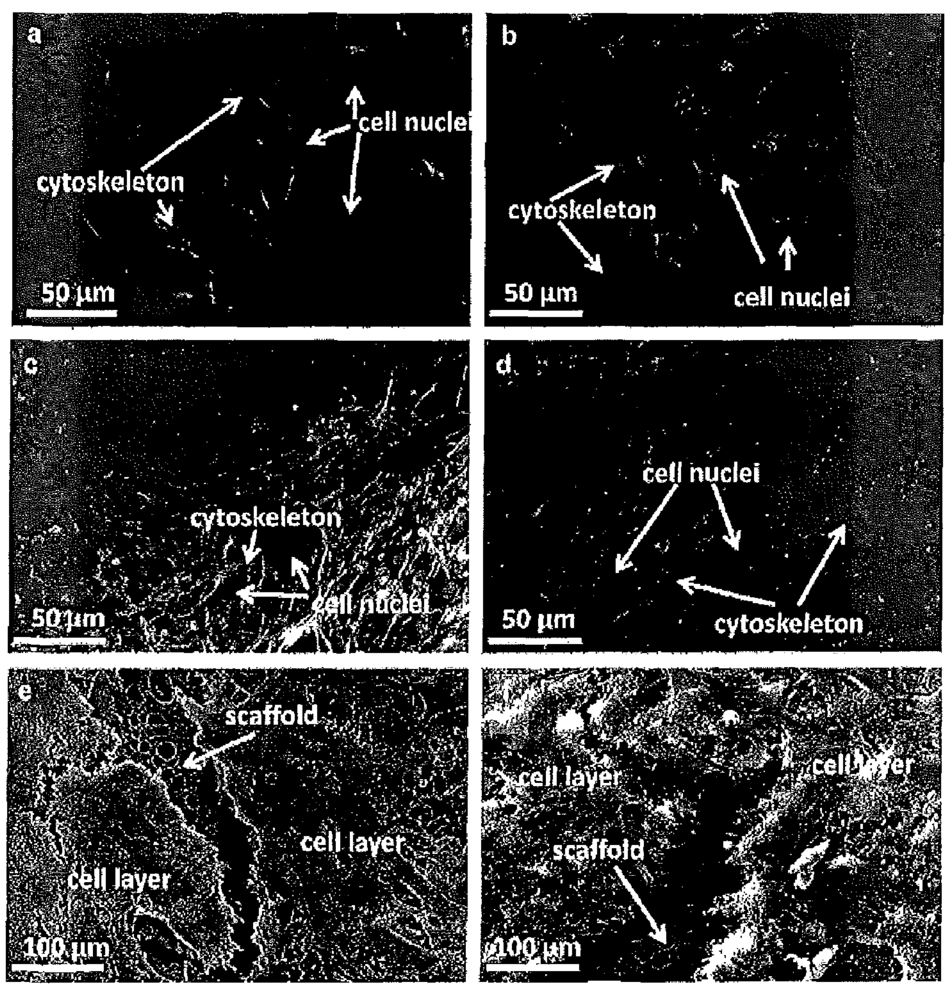
FIG. 22, comprising

In order to assess the morphology and cytoskeletal architecture of 7F2 cells on ND-ODA/PLLA scaffolds, the cells were fixed after 48 h and 6 days post-seeding. Osteoblasts attached, spread, migrated, proliferated to confluence within 6 days (FIG. 21*d* and FIGS. 22*a-d*) and formed nearly identical monolayers on PLLA and ND-ODA/PLLA, scaffolds. Scanning Electron Microscopy (SEM) images (FIGS. 22*e-f*) confirmed these findings: at day 6 post-seeding 7F2 cells have become fully confluent on both scaffolds.

Figure 23:
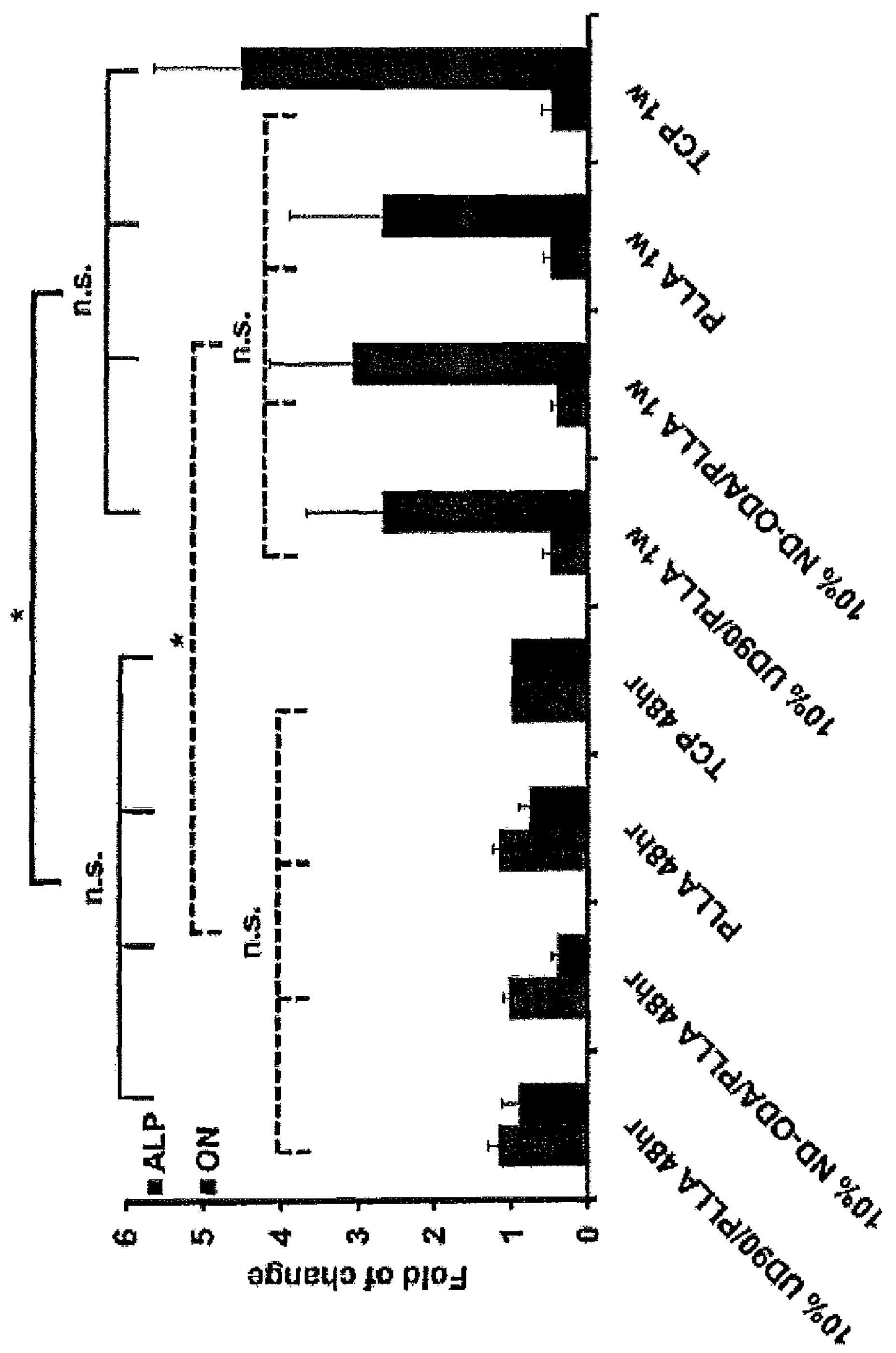
FIG. 23 is a bar graph illustrating real-time quantitative PCR analysis of gene expression for osteogenic marker genes alkaline phosphatase (ALP) and osteocalcin (OCN) in 7F2 osteoblasts cultured for 48 h and 1 week on pure PLLA, 10% wt ND-ODA/PLLA and 10% wt UD90/PLLA post-seeding (*ANOVA: $p<0.05$). Data are expressed in mean±standard error (n=3).

The effect of ND on 7F2 osteoblast differentiation was quantified by RT-PCR for two osteogenic differentiation markers, i.e. ALP and OCN. The relative expression levels of these two genes in 7F2 cells cultured for 48 h and 1 week on three different scaffolds (PLLA, 10% wt ND-ODA/PLLA, and 10% wt UD90/PLLA) were measured and compared to those in 7F2 cells cultured on TCP for 48 h (FIG. 23). Importantly, there was not any significant difference in the expression of osteogenic marker genes on any of the substrates at both 48 and 1 week post-seeding. When comparing the data at one week to those at 48 h, a significant decrease in ALP gene expression was observed concomitant with a significant increase in OCN gene expression ($p<0.05$ by two-way ANOVA). In the present system, the results for both ALP and OCN gene expression levels are in line with the AB assay data, in that there was no significant difference in any of the "biomarkers" on any of the substrates. Taken together, the data from two independent biochemical/molecular assays as well as from immunocytoechemical staining suggested that ND-ODA/PLLA composites with up to 10% wt ND-ODA are non-cytotoxic for 7F2 cells; they support 7F2 cell proliferation and osteogenic differentiation to the same extent as conventional "gold-standards", such as TCP, and therefore may be used for tissue engineering and regenerative medicine.

As illustrated above, ND-ODA/PLLA composites with up to 10% wt ND-ODA showed uniform ND-ODA dispersion and good affinity between the matrix and the filler. The mechanical properties of NDODA/PLLA composites were improved dramatically with the addition of ND-ODA: 1% wt of ND-ODA increased the hardness of the composites by the factor of 4; 10% wt of ND-ODA resulted in almost an order of magnitude higher hardness, 3 times higher Young's modulus, and reduced creep. Cytotoxicity and biocompatibility experiments in concert with osteogenic marker gene expression analysis demonstrated that both ND and ND-ODA are non-toxic to murine osteoblasts, and support cell proliferation and differentiation in vitro. The combination of these properties with intrinsic fluorescence and tunable biodegradability makes the ND-ODA/PLLA composites promising materials for bone tissue engineering and regenerative medicine.

Example 7

Thermal Analysis of ND-ODA/PLLA Composites

Figure 14:
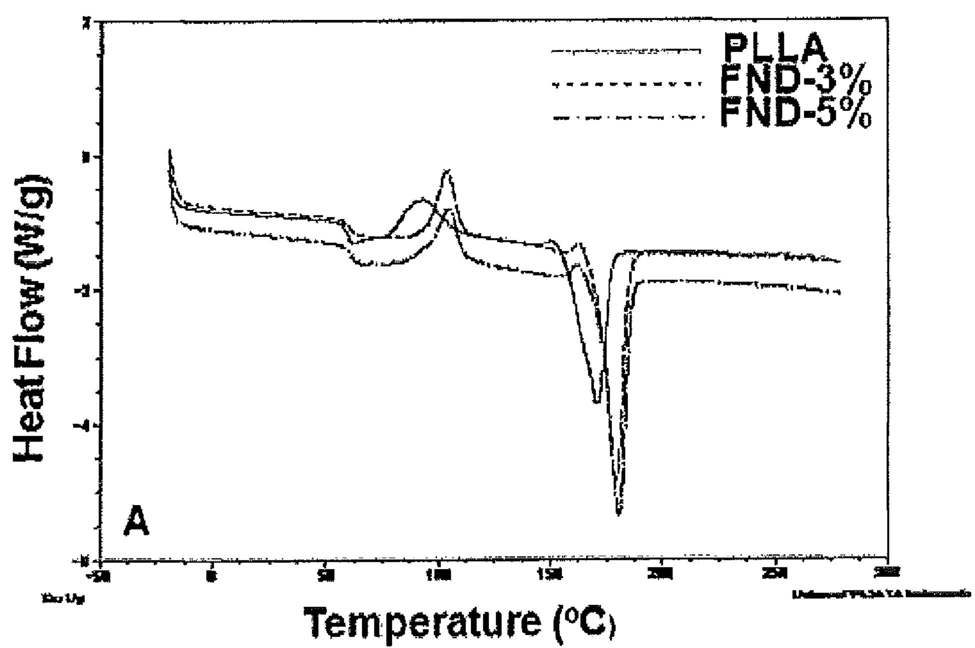
FIG. 14 is a graph that demonstrates the heat flow during DSC measurement of pure PLLA, 3% wt ND-ODA/PLLA and 5% wt ND-ODA/PLLA composites.

In order to test the influence of ND on thermal behavior of PLLA, DSC scans were run for pure PLLA, 3% wt ND-ODA/PLLA, and 5% wt ND-ODA/PLLA composites. The differential heat flow curves of PLLA and ND-ODA/PLLA composites are shown in FIG. 14, indicating no thermal behavior change of the composites when adding ND-ODA into PLLA.

The addition of ND-ODA resulted in a small shift in $T_m$, which could be considered as a machine error. Importantly, there was no phase segregation or secondary peaks visible in ND-ODA/PLLA composites, suggesting that the ND-ODA/PLLA composites with the concentration of nanodiamond no more than 5% wt were homogeneous.

Example 8

GCS Results

Figure 15:
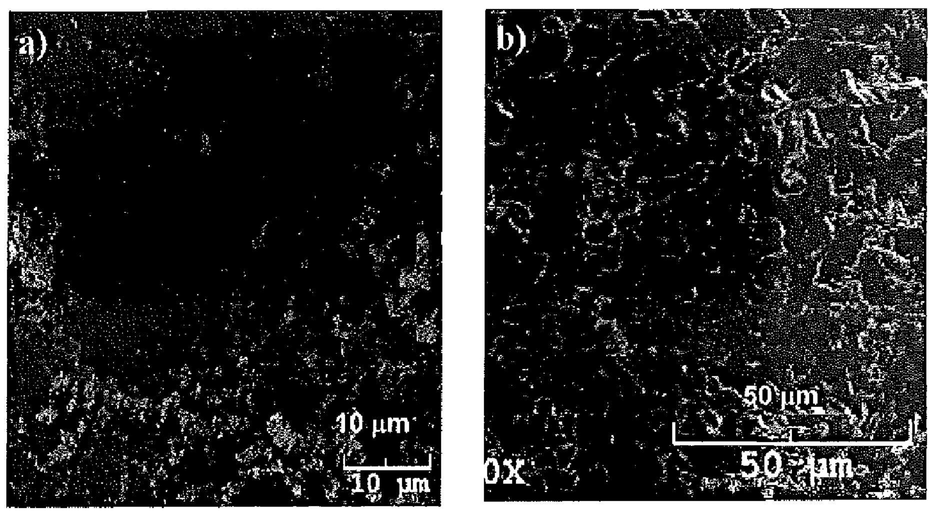
FIG. 15, comprising
Figure 16:
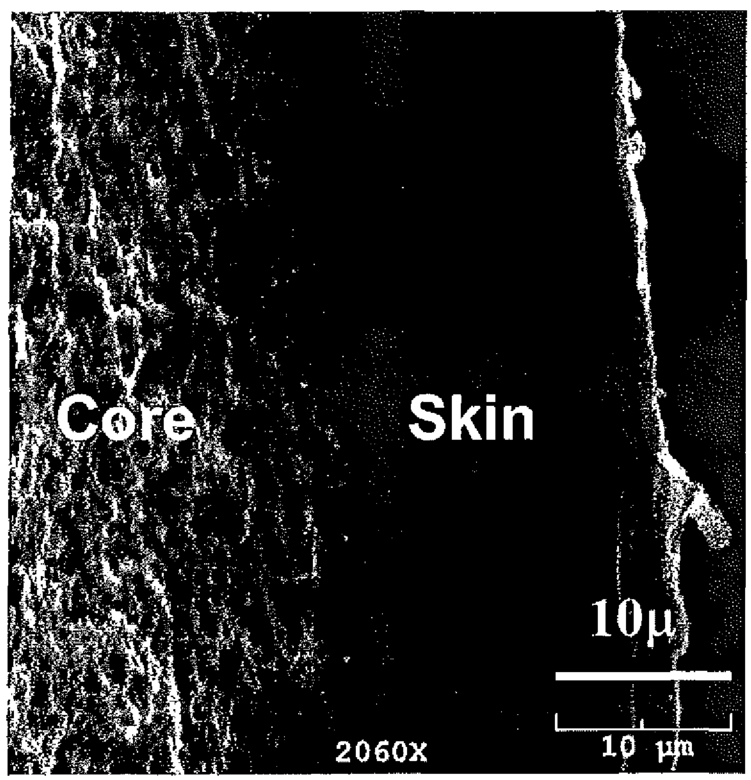
FIG. 16 is an image of a skin-core structure in injection-molded blends.

Polycaprolactone (PCL) and polyethylene oxide (PEO) were used as a model system for the development of continuous, gradient porous structures. The blend was first mixed in a Brabender® batch mixer, resulting in a co-continuous structure, with a phase size in the micrometer range. To produce a structure with continuous pores, the blend was extruded with different dwell times in the extruder for thermal conditioning, and finally selectively dissolved in water and dried. It was found that thermal conditioning can be effectively used to control the phase structure and thus the porous structure of the PCL after dissolution of the PEO phase (FIG. 15). The blend was also injection molded into a cold mold. It was found that, for a 6 mm circular channel, a gradient structure was developed, with finer structure at the surface and coarser structure in the center (FIG. 16).

Example 9

Degradation Test

Degradation experiments were performed by incubating solid cylinders made of PCL, 90/10 and 80/20 PCL-CaP (calcium phosphate) composites in both a physiological buffer (DMEM) and upon admixing blood proteins (DMEM with 10% FBS). The cylinders were harvested at different times, and the molecular weight distribution of partially hydrolyzed polymer was analyzed using high performance liquid chromatography (HPLC, Waters, USA) equipped with a refractive index detector. HPLC measurements were carried out at 25° C. and at a flow rate of 0.8 ml/min using THF (tetrahydrofuran) as an HPLC solvent. Polystyrene standards (Polyscience Co.) were used for calibration.

Figure 17:
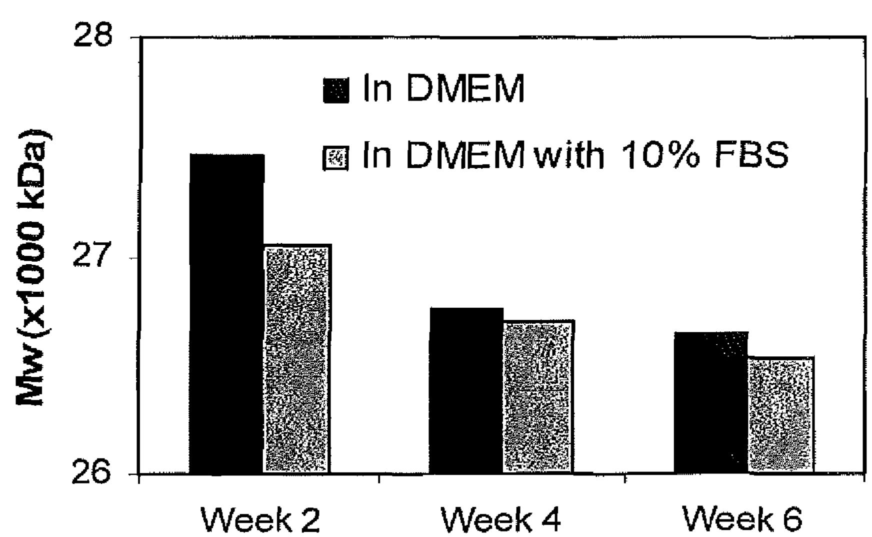
FIG. 17 is a bar graph demonstrating the molecular weight change of composites as a function of incubation time.

The results indicated that the molecular weight of PCL decreased over time and that the effect was more pronounced in the presence of blood proteins (FIG. 17). During the time period of 6 weeks, the observed change was small (<1%) but measurable. The small change was consistent with the fact that PCL has a longer ~2 years degradation time.

INCORPORATION BY REFERENCE

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A nanocomposite material comprising poly-L-lactic acid (PLLA) and 1-10% by weight of octadecylamine-surface-functionalized nanodiamonds (ND-ODA), wherein ND-ODA has the formula of

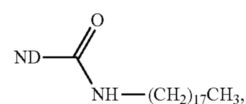

and wherein the Young's modulus of the nanocomposite material is between 5.1 and 8.0 GPa.

2. The nanocomposite material of claim 1, wherein the ND-ODA are prepared by peptide bond formation between octadecylamine and a carboxylate group on the surface-functionalized nanodiamonds.

3. The nanocomposite material of claim 1, further comprising a composition comprising at least one bioactive agent selected from the group consisting of a bone healing drug, growth factor, bone cell, bone stem cell, antibiotic, and anti-inflammatory drug.

4. The nanocomposite material of claim 1, wherein the Meyer's hardness of the nanocomposite material is between 0.20 and 0.51 GPa.

5. The nanocomposite material of claim 1, wherein there is no phase separation of ND-ODA and PLLA.

6. A surgical fixation screw, comprising:

an interconnective porous shell, wherein said shell comprises a nanocomposite material comprising poly-L-lactic acid (PLLA) and 1-10% by weight of octadecylamine-surface-functionalized nanodiamonds (ND-ODA), wherein ND-ODA has the formula of

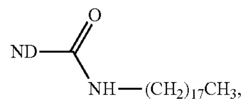

and wherein the Young's modulus of the nanocomposite material is between 5.1 and 8.0 GPa, and a hollow core within said shell, wherein said hollow core is closed on the posterior end of said screw and open on the anterior end of said screw.

7. The surgical fixation screw of claim 6, wherein said hollow core is optionally filled with a composition comprising at least one bioactive agent selected from the group consisting of a bone healing drug, growth factor, bone cell, bone stem cell, antibiotic, and anti-inflammatory drug.

8. The surgical fixation screw of claim 6, wherein said posterior end is tapered with respect to said anterior end.

9. The surgical fixation screw of claim 8, wherein said screw has full-length taper.

10. The surgical fixation screw of claim 6, wherein said anterior end is without head.

11. The surgical fixation screw of claim 6, wherein said posterior end is rounded and blunt.

12. The surgical fixation screw of claim 6, wherein said shell has controllable varying coarseness, whereby phase of said nanocomposite material around said hollow core is coarser than phase of said nanocomposite material on outside surface of said screw.

13. The surgical fixation screw of claim 12, wherein said controllable varying coarseness is achieved through injection molding.

14. A method of performing an orthopedic surgery procedure in a patient, comprising the steps of:

inserting a surgical fixation screw in at least one orifice of a bone or tissue of said patient, wherein said screw comprises:

an interconnective porous shell, wherein said shell comprises a nanocomposite material comprising poly-L-lactic acid (PLLA) and 1-10% by weight of octadecylamine-surface-functionalized nanodiamonds (ND-ODA), wherein ND-ODA has the formula of

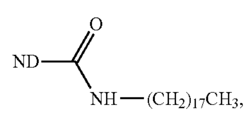

and wherein the Young's modulus of the nanocomposite material is between 5.1 and 8.0 GPa, and a hollow core within said shell, wherein said hollow core is closed on the posterior end of said screw and open on the anterior end of said screw, and filling said hollow core of said screw with a composition comprising at least one bioactive agent selected from the group consisting of a bone healing drug, growth factor, bone cell, bone stem cell, antibiotic, and anti-inflammatory drug.

15. The method of claim 14, wherein said posterior end is tapered with respect to said anterior end.

16. The method of claim 15, wherein said screw has full-length taper.

17. The method of claim 14, wherein said anterior end is without head.

18. The method of claim 14, wherein said posterior end is rounded and blunt.

19. The method of claim 14, wherein said shell has controllable varying coarseness, whereby phase of said nanocomposite material around said hollow core is coarser than phase of said nanocomposite material on outside surface of said screw.

20. The method of claim 19, wherein said controllable varying coarseness is achieved through injection molding.

* * * * *